US008483967B2

(12) United States Patent
Harper

(10) Patent No.: US 8,483,967 B2
(45) Date of Patent: Jul. 9, 2013

(54) METHOD AND SYSTEM FOR PROVIDING REAL TIME ANALYTE SENSOR CALIBRATION WITH RETROSPECTIVE BACKFILL

(75) Inventor: Wesley Scott Harper, Alameda, CA (US)

(73) Assignee: Abbott Diabetes Care Inc., Alameda, CA (US)

(*) Notice: Subject to any disclaimer, the term of this patent is extended or adjusted under 35 U.S.C. 154(b) by 364 days.

(21) Appl. No.: 12/769,635

(22) Filed: Apr. 28, 2010

(65) Prior Publication Data

US 2010/0280782 A1 Nov. 4, 2010

Related U.S. Application Data

(60) Provisional application No. 61/173,600, filed on Apr. 29, 2009.

(51) Int. Cl.
*G01N 33/48* (2006.01)
(52) U.S. Cl.
USPC .................................................. 702/19
(58) Field of Classification Search
USPC .................................................. 702/19
See application file for complete search history.

(56) References Cited

U.S. PATENT DOCUMENTS

| 3,581,062 | A | 5/1971 | Aston |
| 3,926,760 | A | 12/1975 | Allen et al. |
| 3,949,388 | A | 4/1976 | Fuller |
| 4,036,749 | A | 7/1977 | Anderson |
| 4,055,175 | A | 10/1977 | Clemens et al. |
| 4,129,128 | A | 12/1978 | McFarlane |
| 4,245,634 | A | 1/1981 | Albisser et al. |
| 4,327,725 | A | 5/1982 | Cortese et al. |
| 4,344,438 | A | 8/1982 | Schultz |
| 4,349,728 | A | 9/1982 | Phillips et al. |
| 4,373,527 | A | 2/1983 | Fischell |
| 4,392,849 | A | 7/1983 | Petre et al. |
| 4,425,920 | A | 1/1984 | Bourland et al. |
| 4,478,976 | A | 10/1984 | Goertz et al. |
| 4,494,950 | A | 1/1985 | Fischell |
| 4,509,531 | A | 4/1985 | Ward |
| 4,527,240 | A | 7/1985 | Kvitash |
| 4,538,616 | A | 9/1985 | Rogoff |
| 4,619,793 | A | 10/1986 | Lee |
| 4,671,288 | A | 6/1987 | Gough |
| 4,703,756 | A | 11/1987 | Gough et al. |
| 4,731,726 | A | 3/1988 | Allen, III |
| 4,749,985 | A | 6/1988 | Corsberg |
| 4,757,022 | A | 7/1988 | Shults et al. |
| 4,777,953 | A | 10/1988 | Ash et al. |
| 4,779,618 | A | 10/1988 | Mund et al. |
| 4,854,322 | A | 8/1989 | Ash et al. |
| 4,871,351 | A | 10/1989 | Feingold |
| 4,890,620 | A | 1/1990 | Gough |
| 4,925,268 | A | 5/1990 | Iyer et al. |
| 4,953,552 | A | 9/1990 | DeMarzo |
| 4,986,271 | A | 1/1991 | Wilkins |
| 4,995,402 | A | 2/1991 | Smith et al. |
| 5,000,180 | A | 3/1991 | Kuypers et al. |
| 5,002,054 | A | 3/1991 | Ash et al. |
| 5,019,974 | A | 5/1991 | Beckers |
| 5,050,612 | A | 9/1991 | Matsumura |
| 5,055,171 | A | 10/1991 | Peck |
| 5,068,536 | A | 11/1991 | Rosenthal |
| 5,082,550 | A | 1/1992 | Rishpon et al. |
| 5,106,365 | A | 4/1992 | Hernandez |
| 5,122,925 | A | 6/1992 | Inpyn |
| 5,165,407 | A | 11/1992 | Wilson et al. |
| 5,231,988 | A | 8/1993 | Wernicke et al. |
| 5,246,867 | A | 9/1993 | Lakowicz et al. |
| 5,262,035 | A | 11/1993 | Gregg et al. |
| 5,262,305 | A | 11/1993 | Heller et al. |
| 5,264,104 | A | 11/1993 | Gregg et al. |
| 5,264,105 | A | 11/1993 | Gregg et al. |
| 5,279,294 | A | 1/1994 | Anderson et al. |
| 5,285,792 | A | 2/1994 | Sjoquist et al. |
| 5,293,877 | A | 3/1994 | O'Hara et al. |
| 5,299,571 | A | 4/1994 | Mastrototaro |
| 5,320,725 | A | 6/1994 | Gregg et al. |
| 5,322,063 | A | 6/1994 | Allen et al. |
| 5,340,722 | A | 8/1994 | Wolfbeis et al. |
| 5,342,789 | A | 8/1994 | Chick et al. |
| 5,356,786 | A | 10/1994 | Heller et al. |
| 5,360,404 | A | 11/1994 | Novacek et al. |
| 5,372,427 | A | 12/1994 | Padovani et al. |
| 5,379,238 | A | 1/1995 | Stark |
| 5,384,547 | A | 1/1995 | Lynk et al. |
| 5,390,671 | A | 2/1995 | Lord et al. |
| 5,391,250 | A | 2/1995 | Cheney, II et al. |

(Continued)

FOREIGN PATENT DOCUMENTS

| CA | 2468577 | 6/2003 |
| CA | 2678336 | 5/2008 |

(Continued)

OTHER PUBLICATIONS

PCT Application No. PCT/US2010/032863, International Preliminary Report on Patentability and Written Opinion of the International Searching Authority mailed Nov. 10, 2011.

(Continued)

*Primary Examiner* — Jerry Lin
(74) *Attorney, Agent, or Firm* — Jackson & Co., LLP

(57) ABSTRACT

Provided are methods and apparatus for receiving sensor data from an analyte sensor of a sensor monitoring system, processing the received sensor data with time corresponding calibration data, outputting the processed sensor data, detecting one or more adverse conditions associated with the sensor monitoring system, disabling the output of the sensor data during the adverse condition time period, determining that the one or more detected adverse conditions is no longer present in the sensor monitoring system, retrieving the sensor data during the adverse condition time period, processing the retrieved sensor data during the adverse condition time period, and outputting the processed retrieved sensor data.

22 Claims, 7 Drawing Sheets

U.S. PATENT DOCUMENTS

| | | |
|---|---|---|
| 5,408,999 A | 4/1995 | Singh et al. |
| 5,411,647 A | 5/1995 | Johnson et al. |
| 5,425,868 A | 6/1995 | Pedersen |
| 5,431,160 A | 7/1995 | Wilkins |
| 5,431,921 A | 7/1995 | Thombre |
| 5,462,645 A | 10/1995 | Albery et al. |
| 5,497,772 A | 3/1996 | Schulman et al. |
| 5,507,288 A | 4/1996 | Bocker et al. |
| 5,509,410 A | 4/1996 | Hill et al. |
| 5,514,718 A | 5/1996 | Lewis et al. |
| 5,531,878 A | 7/1996 | Vadgama et al. |
| 5,568,806 A | 10/1996 | Cheney, II et al. |
| 5,569,186 A | 10/1996 | Lord et al. |
| 5,582,184 A | 12/1996 | Erickson et al. |
| 5,586,553 A | 12/1996 | Halili et al. |
| 5,593,852 A | 1/1997 | Heller et al. |
| 5,609,575 A | 3/1997 | Larson et al. |
| 5,628,310 A | 5/1997 | Rao et al. |
| 5,653,239 A | 8/1997 | Pompei et al. |
| 5,665,222 A | 9/1997 | Heller et al. |
| 5,711,001 A | 1/1998 | Bussan et al. |
| 5,711,861 A | 1/1998 | Ward et al. |
| 5,733,259 A | 3/1998 | Valcke et al. |
| 5,772,586 A | 6/1998 | Heinonen et al. |
| 5,791,344 A | 8/1998 | Schulman et al. |
| 5,899,855 A | 5/1999 | Brown |
| 5,925,021 A | 7/1999 | Castellano et al. |
| 5,935,224 A | 8/1999 | Svancarek et al. |
| 5,942,979 A | 8/1999 | Luppino |
| 5,957,854 A | 9/1999 | Besson et al. |
| 5,964,993 A | 10/1999 | Blubaugh, Jr. et al. |
| 5,965,380 A | 10/1999 | Heller et al. |
| 5,971,922 A | 10/1999 | Arita et al. |
| 5,995,860 A | 11/1999 | Sun et al. |
| 6,001,067 A | 12/1999 | Shults et al. |
| 6,024,699 A | 2/2000 | Surwit et al. |
| 6,049,727 A | 4/2000 | Crothall |
| 6,083,710 A | 7/2000 | Heller et al. |
| 6,088,608 A | 7/2000 | Schulman et al. |
| 6,091,976 A | 7/2000 | Pfeiffer et al. |
| 6,093,172 A | 7/2000 | Funderburk et al. |
| 6,103,033 A | 8/2000 | Say et al. |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,134,461 A | 10/2000 | Say et al. |
| 6,162,611 A | 12/2000 | Heller et al. |
| 6,175,752 B1 | 1/2001 | Say et al. |
| 6,200,265 B1 | 3/2001 | Walsh et al. |
| 6,212,416 B1 | 4/2001 | Ward et al. |
| 6,219,574 B1 | 4/2001 | Cormier et al. |
| 6,233,471 B1 | 5/2001 | Berner et al. |
| 6,248,067 B1 | 6/2001 | Causey, III et al. |
| 6,275,717 B1 | 8/2001 | Gross et al. |
| 6,284,478 B1 | 9/2001 | Heller et al. |
| 6,293,925 B1 | 9/2001 | Safabash et al. |
| 6,295,506 B1 | 9/2001 | Heinonen et al. |
| 6,306,104 B1 | 10/2001 | Cunningham et al. |
| 6,309,884 B1 | 10/2001 | Cooper et al. |
| 6,329,161 B1 | 12/2001 | Heller et al. |
| 6,360,888 B1 | 3/2002 | McIvor et al. |
| 6,366,794 B1 | 4/2002 | Moussy et al. |
| 6,377,828 B1 | 4/2002 | Chaiken et al. |
| 6,379,301 B1 | 4/2002 | Worthington et al. |
| 6,424,847 B1 | 7/2002 | Mastrototaro et al. |
| 6,427,088 B1 | 7/2002 | Bowman, IV et al. |
| 6,440,068 B1 | 8/2002 | Brown et al. |
| 6,478,736 B1 | 11/2002 | Mault |
| 6,484,046 B1 | 11/2002 | Say et al. |
| 6,514,718 B2 | 2/2003 | Heller et al. |
| 6,544,212 B2 | 4/2003 | Galley et al. |
| 6,551,494 B1 | 4/2003 | Heller et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,576,101 B1 | 6/2003 | Heller et al. |
| 6,577,899 B2 | 6/2003 | Lebel et al. |
| 6,579,690 B1 | 6/2003 | Bonnecaze et al. |
| 6,585,644 B2 | 7/2003 | Lebel et al. |
| 6,591,125 B1 | 7/2003 | Buse et al. |
| 6,595,919 B2 | 7/2003 | Berner et al. |
| 6,605,200 B1 | 8/2003 | Mao et al. |
| 6,605,201 B1 | 8/2003 | Mao et al. |
| 6,607,509 B2 | 8/2003 | Bobroff et al. |
| 6,610,012 B2 | 8/2003 | Mault |
| 6,633,772 B2 | 10/2003 | Ford et al. |
| 6,635,014 B2 | 10/2003 | Starkweather et al. |
| 6,648,821 B2 | 11/2003 | Lebel et al. |
| 6,654,625 B1 | 11/2003 | Say et al. |
| 6,659,948 B2 | 12/2003 | Lebel et al. |
| 6,668,196 B1 | 12/2003 | Villegas et al. |
| 6,687,546 B2 | 2/2004 | Lebel et al. |
| 6,689,056 B1 | 2/2004 | Kilcoyne et al. |
| 6,694,191 B2 | 2/2004 | Starkweather et al. |
| 6,695,860 B1 | 2/2004 | Ward et al. |
| 6,698,269 B2 | 3/2004 | Baber et al. |
| 6,702,857 B2 | 3/2004 | Brauker et al. |
| 6,733,446 B2 | 5/2004 | Lebel et al. |
| 6,740,075 B2 | 5/2004 | Lebel et al. |
| 6,741,877 B1 | 5/2004 | Shults et al. |
| 6,746,582 B2 | 6/2004 | Heller et al. |
| 6,758,810 B2 | 7/2004 | Lebel et al. |
| 6,770,030 B1 | 8/2004 | Schaupp et al. |
| 6,790,178 B1 | 9/2004 | Mault et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,862,465 B2 | 3/2005 | Shults et al. |
| 6,873,268 B2 | 3/2005 | Lebel et al. |
| 6,881,551 B2 | 4/2005 | Heller et al. |
| 6,885,883 B2 | 4/2005 | Parris et al. |
| 6,892,085 B2 | 5/2005 | McIvor et al. |
| 6,895,263 B2 | 5/2005 | Shin et al. |
| 6,895,265 B2 | 5/2005 | Silver |
| 6,931,327 B2 | 8/2005 | Goode, Jr. et al. |
| 6,932,894 B2 | 8/2005 | Mao et al. |
| 6,936,006 B2 | 8/2005 | Sabra |
| 6,950,708 B2 | 9/2005 | Bowman, IV et al. |
| 6,958,705 B2 | 10/2005 | Lebel et al. |
| 6,968,294 B2 | 11/2005 | Gutta et al. |
| 6,971,274 B2 | 12/2005 | Olin |
| 6,974,437 B2 | 12/2005 | Lebel et al. |
| 6,990,366 B2 | 1/2006 | Say et al. |
| 6,997,907 B2 | 2/2006 | Safabash et al. |
| 6,998,247 B2 | 2/2006 | Monfre et al. |
| 7,003,336 B2 | 2/2006 | Holker et al. |
| 7,003,340 B2 | 2/2006 | Say et al. |
| 7,003,341 B2 | 2/2006 | Say et al. |
| 7,022,072 B2 | 4/2006 | Fox et al. |
| 7,024,245 B2 | 4/2006 | Lebel et al. |
| 7,029,444 B2 | 4/2006 | Shin et al. |
| 7,041,068 B2 | 5/2006 | Freeman et al. |
| 7,043,287 B1 | 5/2006 | Khalil et al. |
| 7,052,483 B2 | 5/2006 | Wojcik |
| 7,056,302 B2 | 6/2006 | Douglas |
| 7,074,307 B2 | 7/2006 | Simpson et al. |
| 7,081,195 B2 | 7/2006 | Simpson et al. |
| 7,098,803 B2 | 8/2006 | Mann et al. |
| 7,108,778 B2 | 9/2006 | Simpson et al. |
| 7,110,803 B2 | 9/2006 | Shults et al. |
| 7,113,821 B1 | 9/2006 | Sun et al. |
| 7,118,667 B2 | 10/2006 | Lee |
| 7,134,999 B2 | 11/2006 | Brauker et al. |
| 7,136,689 B2 | 11/2006 | Shults et al. |
| 7,171,274 B2 | 1/2007 | Starkweather et al. |
| 7,190,988 B2 | 3/2007 | Say et al. |
| 7,192,450 B2 | 3/2007 | Brauker et al. |

| | | | | | |
|---|---|---|---|---|---|
| 7,198,606 B2 | 4/2007 | Boecker et al. | 2004/0133164 A1 | 7/2004 | Funderburk et al. |
| 7,225,535 B2 | 6/2007 | Feldman et al. | 2004/0138588 A1 | 7/2004 | Saikley et al. |
| 7,226,978 B2 | 6/2007 | Tapsak et al. | 2004/0146909 A1 | 7/2004 | Duong et al. |
| 7,267,665 B2 | 9/2007 | Steil et al. | 2004/0152622 A1 | 8/2004 | Keith et al. |
| 7,276,029 B2 | 10/2007 | Goode, Jr. et al. | 2004/0167801 A1 | 8/2004 | Say et al. |
| 7,299,082 B2 | 11/2007 | Feldman et al. | 2004/0171921 A1 | 9/2004 | Say et al. |
| 7,310,544 B2 | 12/2007 | Brister et al. | 2004/0176672 A1 | 9/2004 | Silver et al. |
| 7,335,294 B2 | 2/2008 | Heller et al. | 2004/0186362 A1 | 9/2004 | Brauker et al. |
| 7,354,420 B2 | 4/2008 | Steil et al. | 2004/0186365 A1 | 9/2004 | Jin et al. |
| 7,364,592 B2 | 4/2008 | Carr-Brendel et al. | 2004/0193025 A1 | 9/2004 | Steil et al. |
| 7,366,556 B2 | 4/2008 | Brister et al. | 2004/0193090 A1 | 9/2004 | Lebel et al. |
| 7,379,765 B2 | 5/2008 | Petisce et al. | 2004/0197846 A1 | 10/2004 | Hockersmith et al. |
| 7,401,111 B1 | 7/2008 | Batman et al. | 2004/0199059 A1 | 10/2004 | Brauker et al. |
| 7,402,153 B2 | 7/2008 | Steil et al. | 2004/0204687 A1 | 10/2004 | Mogensen et al. |
| 7,424,318 B2 | 9/2008 | Brister et al. | 2004/0225338 A1 | 11/2004 | Lebel et al. |
| 7,460,898 B2 | 12/2008 | Brister et al. | 2004/0236200 A1 | 11/2004 | Say et al. |
| 7,467,003 B2 | 12/2008 | Brister et al. | 2004/0254433 A1 | 12/2004 | Bandis et al. |
| 7,471,972 B2 | 12/2008 | Rhodes et al. | 2004/0267300 A1 | 12/2004 | Mace |
| 7,494,465 B2 | 2/2009 | Brister et al. | 2005/0004439 A1 | 1/2005 | Shin et al. |
| 7,497,827 B2 | 3/2009 | Brister et al. | 2005/0004494 A1 | 1/2005 | Perez et al. |
| 7,519,408 B2 | 4/2009 | Rasdal et al. | 2005/0010269 A1 | 1/2005 | Lebel et al. |
| 7,547,281 B2 | 6/2009 | Hayes et al. | 2005/0027177 A1 | 2/2005 | Shin et al. |
| 7,569,030 B2 | 8/2009 | Lebel et al. | 2005/0031689 A1 | 2/2005 | Shults et al. |
| 7,583,990 B2 | 9/2009 | Goode, Jr. et al. | 2005/0038332 A1 | 2/2005 | Saidara et al. |
| 7,591,801 B2 | 9/2009 | Brauker et al. | 2005/0043598 A1 | 2/2005 | Goode, Jr. et al. |
| 7,599,726 B2 | 10/2009 | Goode, Jr. et al. | 2005/0090607 A1 | 4/2005 | Tapsak et al. |
| 7,613,491 B2 | 11/2009 | Boock et al. | 2005/0096511 A1 | 5/2005 | Fox et al. |
| 7,615,007 B2 | 11/2009 | Shults et al. | 2005/0096512 A1 | 5/2005 | Fox et al. |
| 7,618,369 B2 | 11/2009 | Hayter et al. | 2005/0112169 A1 | 5/2005 | Brauker et al. |
| 7,632,228 B2 | 12/2009 | Brauker et al. | 2005/0113653 A1 | 5/2005 | Fox et al. |
| 7,637,868 B2 | 12/2009 | Saint et al. | 2005/0114068 A1 | 5/2005 | Chey et al. |
| 7,640,048 B2 | 12/2009 | Dobbles et al. | 2005/0121322 A1 | 6/2005 | Say et al. |
| 7,651,596 B2 | 1/2010 | Petisce et al. | 2005/0131346 A1 | 6/2005 | Douglas |
| 7,654,956 B2 | 2/2010 | Brister et al. | 2005/0143635 A1 | 6/2005 | Kamath et al. |
| 7,657,297 B2 | 2/2010 | Simpson et al. | 2005/0176136 A1 | 8/2005 | Burd et al. |
| 7,711,402 B2 | 5/2010 | Shults et al. | 2005/0177398 A1 | 8/2005 | Watanabe et al. |
| 7,713,574 B2 | 5/2010 | Brister et al. | 2005/0182306 A1 | 8/2005 | Sloan |
| 7,715,893 B2 | 5/2010 | Kamath et al. | 2005/0187720 A1 | 8/2005 | Goode, Jr. et al. |
| 7,826,981 B2 | 11/2010 | Goode et al. | 2005/0192494 A1 | 9/2005 | Ginsberg |
| 7,885,698 B2 | 2/2011 | Feldman et al. | 2005/0192557 A1 | 9/2005 | Brauker et al. |
| 7,912,655 B2 | 3/2011 | Power et al. | 2005/0195930 A1 | 9/2005 | Spital et al. |
| 7,912,674 B2 | 3/2011 | Killoren Clark et al. | 2005/0199494 A1 | 9/2005 | Say et al. |
| 7,928,850 B2 | 4/2011 | Hayter et al. | 2005/0203360 A1 | 9/2005 | Brauker et al. |
| 7,976,467 B2 | 7/2011 | Young et al. | 2005/0239154 A1 | 10/2005 | Feldman et al. |
| 8,066,639 B2 | 11/2011 | Nelson et al. | 2005/0241957 A1 | 11/2005 | Mao et al. |
| 2002/0019022 A1 | 2/2002 | Dunn et al. | 2005/0245795 A1 | 11/2005 | Goode, Jr. et al. |
| 2002/0042090 A1 | 4/2002 | Heller et al. | 2005/0245799 A1 | 11/2005 | Brauker et al. |
| 2002/0095076 A1 | 7/2002 | Krausman et al. | 2005/0245839 A1 | 11/2005 | Stivoric et al. |
| 2002/0103499 A1 | 8/2002 | Perez et al. | 2005/0245904 A1 | 11/2005 | Estes et al. |
| 2002/0106709 A1 | 8/2002 | Potts et al. | 2005/0287620 A1 | 12/2005 | Heller et al. |
| 2002/0128594 A1 | 9/2002 | Das et al. | 2006/0001538 A1 | 1/2006 | Kraft et al. |
| 2002/0161288 A1 | 10/2002 | Shin et al. | 2006/0004270 A1 | 1/2006 | Bedard et al. |
| 2002/0169635 A1 | 11/2002 | Shillingburg | 2006/0015020 A1 | 1/2006 | Neale et al. |
| 2003/0004403 A1 | 1/2003 | Drinan et al. | 2006/0015024 A1 | 1/2006 | Brister et al. |
| 2003/0023317 A1 | 1/2003 | Brauker et al. | 2006/0016700 A1 | 1/2006 | Brister et al. |
| 2003/0032874 A1 | 2/2003 | Rhodes et al. | 2006/0019327 A1 | 1/2006 | Brister et al. |
| 2003/0042137 A1 | 3/2003 | Mao et al. | 2006/0020186 A1 | 1/2006 | Brister et al. |
| 2003/0065308 A1 | 4/2003 | Lebel et al. | 2006/0020187 A1 | 1/2006 | Brister et al. |
| 2003/0100821 A1 | 5/2003 | Heller et al. | 2006/0020188 A1 | 1/2006 | Kamath et al. |
| 2003/0125612 A1 | 7/2003 | Fox et al. | 2006/0020189 A1 | 1/2006 | Brister et al. |
| 2003/0130616 A1 | 7/2003 | Steil et al. | 2006/0020190 A1 | 1/2006 | Kamath et al. |
| 2003/0134347 A1 | 7/2003 | Heller et al. | 2006/0020191 A1 | 1/2006 | Brister et al. |
| 2003/0168338 A1 | 9/2003 | Gao et al. | 2006/0020192 A1 | 1/2006 | Brister et al. |
| 2003/0176933 A1 | 9/2003 | Lebel et al. | 2006/0029177 A1 | 2/2006 | Cranford, Jr. et al. |
| 2003/0187338 A1 | 10/2003 | Say et al. | 2006/0031094 A1 | 2/2006 | Cohen et al. |
| 2003/0199790 A1 | 10/2003 | Boecker et al. | 2006/0036139 A1 | 2/2006 | Brister et al. |
| 2003/0208113 A1 | 11/2003 | Mault et al. | 2006/0036140 A1 | 2/2006 | Brister et al. |
| 2003/0212317 A1 | 11/2003 | Kovatchev et al. | 2006/0036141 A1 | 2/2006 | Kamath et al. |
| 2003/0212379 A1 | 11/2003 | Bylund et al. | 2006/0036142 A1 | 2/2006 | Brister et al. |
| 2003/0216630 A1 | 11/2003 | Jersey-Willuhn et al. | 2006/0036143 A1 | 2/2006 | Brister et al. |
| 2003/0217966 A1 | 11/2003 | Tapsak et al. | 2006/0036144 A1 | 2/2006 | Brister et al. |
| 2004/0010207 A1 | 1/2004 | Flaherty et al. | 2006/0036145 A1 | 2/2006 | Brister et al. |
| 2004/0011671 A1 | 1/2004 | Shults et al. | 2006/0155180 A1 | 7/2006 | Brister et al. |
| 2004/0039298 A1 | 2/2004 | Abreu | 2006/0166629 A1 | 7/2006 | Reggiardo |
| 2004/0040840 A1 | 3/2004 | Mao et al. | 2006/0173260 A1 | 8/2006 | Gaoni et al. |
| 2004/0045879 A1 | 3/2004 | Shults et al. | 2006/0173406 A1 | 8/2006 | Hayes et al. |
| 2004/0064068 A1 | 4/2004 | DeNuzzio et al. | 2006/0173444 A1 | 8/2006 | Choy et al. |
| 2004/0106858 A1 | 6/2004 | Say et al. | 2006/0183985 A1 | 8/2006 | Brister et al. |
| 2004/0122353 A1 | 6/2004 | Shahmirian et al. | 2006/0189863 A1 | 8/2006 | Peyser et al. |

| | | |
|---|---|---|
| 2006/0222566 A1 | 10/2006 | Brauker et al. |
| 2006/0224109 A1 | 10/2006 | Steil et al. |
| 2006/0229512 A1 | 10/2006 | Petisce et al. |
| 2006/0247508 A1 | 11/2006 | Fennell |
| 2006/0272652 A1 | 12/2006 | Stocker et al. |
| 2007/0016381 A1 | 1/2007 | Kamath et al. |
| 2007/0027381 A1 | 2/2007 | Stafford |
| 2007/0032706 A1 | 2/2007 | Kamath et al. |
| 2007/0033074 A1 | 2/2007 | Nitzan et al. |
| 2007/0038053 A1 | 2/2007 | Berner et al. |
| 2007/0060814 A1 | 3/2007 | Stafford |
| 2007/0066873 A1 | 3/2007 | Kamath et al. |
| 2007/0071681 A1 | 3/2007 | Gadkar et al. |
| 2007/0073129 A1 | 3/2007 | Shah et al. |
| 2007/0078314 A1 | 4/2007 | Grounsell et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0078323 A1 | 4/2007 | Reggiardo et al. |
| 2007/0106135 A1 | 5/2007 | Sloan et al. |
| 2007/0124002 A1 | 5/2007 | Estes et al. |
| 2007/0149875 A1 | 6/2007 | Ouyang et al. |
| 2007/0163880 A1 | 7/2007 | Woo et al. |
| 2007/0168224 A1 | 7/2007 | Letzt et al. |
| 2007/0173706 A1 | 7/2007 | Neinast et al. |
| 2007/0173761 A1 | 7/2007 | Kanderian et al. |
| 2007/0179349 A1 | 8/2007 | Hoyme et al. |
| 2007/0179352 A1 | 8/2007 | Randlov et al. |
| 2007/0191701 A1 | 8/2007 | Feldman et al. |
| 2007/0203407 A1 | 8/2007 | Hoss et al. |
| 2007/0203966 A1 | 8/2007 | Brauker et al. |
| 2007/0232880 A1 | 10/2007 | Siddiqui et al. |
| 2007/0235331 A1 | 10/2007 | Simpson et al. |
| 2007/0249922 A1 | 10/2007 | Peyser et al. |
| 2008/0009692 A1 | 1/2008 | Stafford |
| 2008/0017522 A1 | 1/2008 | Heller et al. |
| 2008/0021666 A1 | 1/2008 | Goode, Jr. et al. |
| 2008/0029391 A1 | 2/2008 | Mao et al. |
| 2008/0033254 A1 | 2/2008 | Kamath et al. |
| 2008/0039702 A1 | 2/2008 | Hayter et al. |
| 2008/0045824 A1 | 2/2008 | Tapsak et al. |
| 2008/0058625 A1 | 3/2008 | McGarraugh et al. |
| 2008/0064937 A1 | 3/2008 | McGarraugh et al. |
| 2008/0071156 A1 | 3/2008 | Brister et al. |
| 2008/0071157 A1 | 3/2008 | McGarraugh et al. |
| 2008/0071158 A1 | 3/2008 | McGarraugh et al. |
| 2008/0071580 A1 | 3/2008 | Marcus |
| 2008/0081977 A1 | 4/2008 | Hayter et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0097289 A1 | 4/2008 | Steil et al. |
| 2008/0108942 A1 | 5/2008 | Brister et al. |
| 2008/0154513 A1 | 6/2008 | Kovatchev et al. |
| 2008/0167543 A1 | 7/2008 | Say et al. |
| 2008/0172205 A1 | 7/2008 | Breton et al. |
| 2008/0183060 A1 | 7/2008 | Steil et al. |
| 2008/0183061 A1 | 7/2008 | Goode et al. |
| 2008/0183399 A1 | 7/2008 | Goode et al. |
| 2008/0188731 A1 | 8/2008 | Brister et al. |
| 2008/0188796 A1 | 8/2008 | Steil et al. |
| 2008/0189051 A1 | 8/2008 | Goode et al. |
| 2008/0194935 A1 | 8/2008 | Brister et al. |
| 2008/0194936 A1 | 8/2008 | Goode et al. |
| 2008/0194937 A1 | 8/2008 | Goode et al. |
| 2008/0194938 A1 | 8/2008 | Brister et al. |
| 2008/0195232 A1 | 8/2008 | Carr-Brendel et al. |
| 2008/0195967 A1 | 8/2008 | Goode et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0208025 A1 | 8/2008 | Shults et al. |
| 2008/0208113 A1 | 8/2008 | Damiano et al. |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0234992 A1 | 9/2008 | Pinaki et al. |
| 2008/0242961 A1 | 10/2008 | Brister et al. |
| 2008/0255434 A1 | 10/2008 | Hayter et al. |
| 2008/0255437 A1 | 10/2008 | Hayter |
| 2008/0255438 A1 | 10/2008 | Saudara et al. |
| 2008/0255808 A1 | 10/2008 | Hayter |
| 2008/0256048 A1 | 10/2008 | Hayter |
| 2008/0262469 A1 | 10/2008 | Brister et al. |
| 2008/0275313 A1 | 11/2008 | Brister et al. |
| 2008/0278331 A1 | 11/2008 | Hayter et al. |
| 2008/0287755 A1 | 11/2008 | Sass et al. |
| 2008/0287761 A1 | 11/2008 | Hayter et al. |
| 2008/0287762 A1 | 11/2008 | Hayter |
| 2008/0287763 A1 | 11/2008 | Hayter |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0288180 A1 | 11/2008 | Hayter |
| 2008/0288204 A1 | 11/2008 | Hayter et al. |
| 2008/0296155 A1 | 12/2008 | Shults et al. |
| 2008/0300572 A1 | 12/2008 | Rankers et al. |
| 2008/0306368 A1 | 12/2008 | Goode et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2008/0312841 A1 | 12/2008 | Hayter |
| 2008/0312842 A1 | 12/2008 | Hayter |
| 2008/0312844 A1 | 12/2008 | Hayter et al. |
| 2008/0312845 A1 | 12/2008 | Hayter et al. |
| 2009/0005665 A1 | 1/2009 | Hayter et al. |
| 2009/0006034 A1 | 1/2009 | Hayter et al. |
| 2009/0012379 A1 | 1/2009 | Goode et al. |
| 2009/0018424 A1 | 1/2009 | Kamath et al. |
| 2009/0018425 A1 | 1/2009 | Ouyang et al. |
| 2009/0030294 A1 | 1/2009 | Petisce et al. |
| 2009/0033482 A1 | 2/2009 | Hayter et al. |
| 2009/0036747 A1 | 2/2009 | Hayter et al. |
| 2009/0036758 A1 | 2/2009 | Brauker et al. |
| 2009/0036760 A1 | 2/2009 | Hayter |
| 2009/0036763 A1 | 2/2009 | Brauker et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0054750 A1 | 2/2009 | Jennewine |
| 2009/0055149 A1 | 2/2009 | Hayter et al. |
| 2009/0062633 A1 | 3/2009 | Brauker et al. |
| 2009/0062635 A1 | 3/2009 | Brauker et al. |
| 2009/0062767 A1 | 3/2009 | VanAntwerp et al. |
| 2009/0063402 A1 | 3/2009 | Hayter |
| 2009/0076356 A1 | 3/2009 | Simpson et al. |
| 2009/0076360 A1 | 3/2009 | Brister et al. |
| 2009/0076361 A1 | 3/2009 | Kamath et al. |
| 2009/0099436 A1 | 4/2009 | Brister et al. |
| 2009/0105570 A1 | 4/2009 | Sloan et al. |
| 2009/0105636 A1 | 4/2009 | Hayter et al. |
| 2009/0112154 A1 | 4/2009 | Montgomery et al. |
| 2009/0124877 A1 | 5/2009 | Goode, Jr. et al. |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0156919 A1 | 6/2009 | Brister et al. |
| 2009/0156924 A1 | 6/2009 | Shariati et al. |
| 2009/0157430 A1 | 6/2009 | Rule et al. |
| 2009/0163790 A1 | 6/2009 | Brister et al. |
| 2009/0163791 A1 | 6/2009 | Brister et al. |
| 2009/0164190 A1 | 6/2009 | Hayter |

| | | |
|---|---|---|
| 2009/0164239 A1 | 6/2009 | Hayter et al. |
| 2009/0164251 A1 | 6/2009 | Hayter |
| 2009/0178459 A1 | 7/2009 | Li et al. |
| 2009/0182217 A1 | 7/2009 | Li et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0198118 A1 | 8/2009 | Hayter et al. |
| 2009/0203981 A1 | 8/2009 | Brauker et al. |
| 2009/0204341 A1 | 8/2009 | Brauker et al. |
| 2009/0210249 A1 | 8/2009 | Rasch-Menges et al. |
| 2009/0216103 A1 | 8/2009 | Brister et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0247857 A1 | 10/2009 | Harper et al. |
| 2009/0287073 A1 | 11/2009 | Boock et al. |
| 2009/0287074 A1 | 11/2009 | Shults et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0010324 A1 | 1/2010 | Brauker et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0030038 A1 | 2/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049024 A1 | 2/2010 | Saint et al. |
| 2010/0057040 A1 | 3/2010 | Hayter |
| 2010/0057041 A1 | 3/2010 | Hayter |
| 2010/0057042 A1 | 3/2010 | Hayter |
| 2010/0057044 A1 | 3/2010 | Hayter |
| 2010/0057057 A1 | 3/2010 | Hayter et al. |
| 2010/0063373 A1 | 3/2010 | Kamath et al. |
| 2010/0076283 A1 | 3/2010 | Simpson et al. |
| 2010/0081906 A1 | 4/2010 | Hayter et al. |
| 2010/0081908 A1 | 4/2010 | Dobbles et al. |
| 2010/0081910 A1 | 4/2010 | Brister et al. |
| 2010/0087724 A1 | 4/2010 | Brauker et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0119693 A1 | 5/2010 | Tapsak et al. |
| 2010/0121169 A1 | 5/2010 | Petisce et al. |
| 2010/0152548 A1 | 6/2010 | Koski |
| 2010/0160757 A1 | 6/2010 | Weinert et al. |
| 2010/0191085 A1 | 7/2010 | Budiman |
| 2010/0191087 A1 | 7/2010 | Talbot et al. |
| 2010/0191472 A1 | 7/2010 | Doniger et al. |
| 2010/0204557 A1 | 8/2010 | Kiaie et al. |
| 2010/0234710 A1 | 9/2010 | Budiman et al. |
| 2010/0259543 A1 | 10/2010 | Tarassenko et al. |
| 2010/0274515 A1 | 10/2010 | Hoss et al. |
| 2010/0331651 A1 | 12/2010 | Groll |
| 2011/0004085 A1 | 1/2011 | Mensinger et al. |
| 2011/0021889 A1 | 1/2011 | Hoss et al. |
| 2011/0077469 A1 | 3/2011 | Blocker et al. |
| 2011/0123971 A1 | 5/2011 | Berkowitz et al. |
| 2011/0137571 A1 | 6/2011 | Power et al. |
| 2011/0184752 A1 | 7/2011 | Ray et al. |
| 2011/0208027 A1 | 8/2011 | Wagner et al. |
| 2011/0263959 A1 | 10/2011 | Young et al. |
| 2011/0264378 A1 | 10/2011 | Breton et al. |

FOREIGN PATENT DOCUMENTS

| | | |
|---|---|---|
| CA | 2626349 | 9/2008 |
| CA | 2728831 | 7/2011 |
| CA | 2617965 | 10/2011 |
| DE | 4401400 | 7/1995 |
| EP | 0098592 | 1/1984 |
| EP | 0127958 | 12/1984 |
| EP | 0320109 | 6/1989 |
| EP | 0353328 | 2/1990 |
| EP | 0390390 | 10/1990 |
| EP | 0396788 | 11/1990 |
| EP | 0286118 | 1/1995 |
| EP | 1048264 | 11/2000 |
| EP | 2031534 | 3/2009 |
| EP | 1725163 | 12/2010 |
| WO | WO-96/25089 | 8/1996 |
| WO | WO-96/35370 | 11/1996 |
| WO | WO-98/35053 | 8/1998 |
| WO | WO-99/27849 | 6/1999 |
| WO | WO-99/28736 | 6/1999 |
| WO | WO-99/56613 | 11/1999 |
| WO | WO-00/49940 | 8/2000 |
| WO | WO-00/59370 | 10/2000 |
| WO | WO-00/78992 | 12/2000 |
| WO | WO-01/52935 | 7/2001 |
| WO | WO-01/54753 | 8/2001 |
| WO | WO-02/16905 | 2/2002 |
| WO | WO-02/058537 | 8/2002 |
| WO | WO-03/057027 | 7/2003 |
| WO | WO-03/076893 | 9/2003 |
| WO | WO-03/082091 | 10/2003 |
| WO | WO-03/085372 | 10/2003 |
| WO | WO-2004/061420 | 7/2004 |
| WO | WO-2005/041766 | 5/2005 |
| WO | WO-2005/057175 | 6/2005 |
| WO | WO-2005/065538 | 7/2005 |
| WO | WO-2005/089103 | 9/2005 |
| WO | WO-2006/020212 | 2/2006 |
| WO | WO-2006/024671 | 3/2006 |
| WO | WO-2006/072035 | 7/2006 |
| WO | WO-2006/079114 | 7/2006 |
| WO | WO-2006/118947 | 11/2006 |
| WO | WO-2007/016399 | 2/2007 |
| WO | WO-2007/019289 | 2/2007 |
| WO | WO-2007/027788 | 3/2007 |
| WO | WO-2007/041069 | 4/2007 |
| WO | WO-2007/041070 | 4/2007 |
| WO | WO-2007/041248 | 4/2007 |
| WO | WO-2007/056638 | 5/2007 |
| WO | WO-2007/101223 | 9/2007 |
| WO | WO-2007/120363 | 10/2007 |
| WO | WO-2007/126444 | 11/2007 |
| WO | WO-2007/053832 | 12/2007 |
| WO | WO-2007/143225 | 12/2007 |
| WO | WO-2008/021913 | 2/2008 |
| WO | WO-2008/042760 | 4/2008 |
| WO | WO-2008/048452 | 4/2008 |
| WO | WO-2008/052374 | 5/2008 |
| WO | WO-2008/062099 | 5/2008 |
| WO | WO-2008/128210 | 10/2008 |
| WO | WO-2008/130896 | 10/2008 |
| WO | WO-2008/130897 | 10/2008 |
| WO | WO-2008/130898 | 10/2008 |
| WO | WO-2008/143943 | 11/2008 |
| WO | WO-2008/144445 | 11/2008 |
| WO | WO-2009/018058 | 2/2009 |
| WO | WO-2009/086216 | 7/2009 |
| WO | WO-2009/096992 | 8/2009 |
| WO | WO-2009/097594 | 8/2009 |
| WO | WO-2010/062898 | 6/2010 |
| WO | WO-2011/000528 | 1/2011 |
| WO | WO-2011/104616 | 9/2011 |

OTHER PUBLICATIONS

Armour, J. C., et al., "Application of Chronic Intravascular Blood Glucose Sensor in Dogs", *Diabetes*, vol. 39, 1990, pp. 1519-1526.

Bennion, N., et al., "Alternate Site Glucose Testing: A Crossover Design", *Diabetes Technology & Therapeutics*, vol. 4, No. 1, 2002, pp. 25-33.

Blank, T. B., et al., "Clinical Results From a Non-Invasive Blood Glucose Monitor", *Optical Diagnostics and Sensing of Biological Fluids and Glucose and Cholesterol Monitoring II*, Proceedings of SPIE, vol. 4624, 2002, pp. 1-10.

Brooks, S. L., et al., "Development of an On-Line Glucose Sensor for Fermentation Monitoring", *Biosensors*, vol. 3, 1987/88, pp. 45-56.

Cass, A. E., et al., "Ferrocene-Medicated Enzyme Electrode for Amperometric Determination of Glucose", *Analytical Chemistry*, vol. 56, No. 4, 1984, 667-671.

Csoregi, E., et al., "Design and Optimization of a Selective Subcutaneously Implantable Glucose Electrode Based on 'Wired' Glucose Oxidase", *Analytical Chemistry*, vol. 67, No. 7, 1995, pp. 1240-1244.

El-Khatib, F. H, et al., "Adaptive Closed-Loop Control Provides Blood-Glucose Regulation Using Subcutaneous Insulin and Glucagon Infusion in Diabetic Swine", *Journal of Diabetes Science and Technology*, vol. 1, No. 2, 2007, pp. 181-192.

Feldman, B., et al., "A Continuous Glucose Sensor Based on Wired Enzyme™ Technology—Results from a 3-Day Trial in Patients with Type 1 Diabetes", *Diabetes Technology & Therapeutics*, vol. 5, No. 5, 2003, pp. 769-779.

Feldman, B., et al., "Correlation of Glucose Concentrations in Interstitial Fluid and Venous Blood During Periods of Rapid Glucose Change", *Abbott Diabetes Care, Inc. Freestyle Navigator Continuous Glucose Monitor Pamphlet*, 2004.

Isermann, R., "Supervision, Fault-Detection and Fault-Diagnosis Methods—An Introduction", *Control Engineering Practice*, vol. 5, No. 5, 1997, pp. 639-652.

Isermann, R., et al., "Trends in the Application of Model-Based Fault Detection and Diagnosis of Technical Processes", *Control Engineering Practice*, vol. 5, No. 5, 1997, pp. 709-719.

Johnson, P. C., "Peripheral Circulation", *John Wiley & Sons*, 1978, pp. 198.

Jungheim, K., et al., "How Rapid Does Glucose Concentration Change in Daily Life of Patients with Type 1 Diabetes?", 2002, pp. 250.

Jungheim, K., et al., "Risky Delay of Hypoglycemia Detection by Glucose Monitoring at the Arm", *Diabetes Care*, vol. 24, No. 7, 2001, pp. 1303-1304.

Kaplan, S. M., "Wiley Electrical and Electronics Engineering Dictionary", *IEEE Press*, 2004, pp. 141, 142, 548, 549.

Lortz, J., et al., "What is Bluetooth? We Explain the Newest Short-Range Connectivity Technology", *Smart Computing Learning Series, Wireless Computing*, vol. 8, Issue 5, 2002, pp. 72-74.

Malin, S. F., et al., "Noninvasive Prediction of Glucose by Near-Infrared Diffuse Reflectance Spectoscopy", *Clinical Chemistry*, vol. 45, No. 9, 1999, pp. 1651-1658.

McGarraugh, G., et al., "Glucose Measurements Using Blood Extracted from the Forearm and the Finger", *TheraSense*, Inc., 2001, 16 Pages.

McGarraugh, G., et al., "Physiological Influences on Off-Finger Glucose Testing", *Diabetes Technology & Therapeutics*, vol. 3, No. 3, 2001, pp. 367-376.

McKean, B. D., et al., "A Telemetry-Instrumentation System for Chronically Implanted Glucose and Oxygen Sensors", *IEEE Transactions on Biomedical Engineering*, vol. 35, No. 7, 1988, pp. 526-532.

Pickup, J., et al., "Implantable Glucose Sensors: Choosing the Appropriate Sensing Strategy", *Biosensors*, vol. 3, 1987/88, pp. 335-346.

Pickup, J., et al., "In Vivo Molecular Sensing in Diabetes Mellitus: An Implantable Glucose Sensor with Direct Electron Transfer", *Diabetologia*, vol. 32, 1989, pp. 213-217.

Pishko, M. V., et al., "Amperometric Glucose Microelectrodes Prepared Through Immobilization of Glucose Oxidase in Redox Hydrogels", *Analytical Chemistry*, vol. 63, No. 20, 1991, pp. 2268-2272.

Quinn, C. P., et al., "Kinetics of Glucose Delivery to Subcutaneous Tissue in Rats Measured with 0.3-mm Amperometric Microsensors", *The American Physiological Society*, 1995, E155-E161.

Roe, J. N., et al., "Bloodless Glucose Measurements", *Critical Review in Therapeutic Drug Carrier Systems*, vol. 15, Issue 3, 1998, pp. 199-241.

Sakakida, M., et al., "Development of Ferrocene-Mediated Needle-Type Glucose Sensor as a Measure of True Subcutaneous Tissue Glucose Concentrations", *Artificial Organs Today*, vol. 2, No. 2, 1992, pp. 145-158.

Sakakida, M., et al., "Ferrocene-Mediated Needle-Type Glucose Sensor Covered with Newly Designed Biocompatible Membrane", *Sensors and Actuators B*, vol. 13-14, 1993, pp. 319-322.

Salehi, C., et al., "A Telemetry-Instrumentation System for Long-Term Implantable Glucose and Oxygen Sensors", *Analytical Letters*, vol. 29, No. 13, 1996, pp. 2289-2308.

Schmidtke, D. W., et al., "Measurement and Modeling of the Transient Difference Between Blood and Subcutaneous Glucose Concentrations in the Rat After Injection of Insulin", *Proceedings of the National Academy of Sciences*, vol. 95, 1998, pp. 294-299.

Shaw, G. W., et al., "In Vitro Testing of a Simply Constructed, Highly Stable Glucose Sensor Suitable for Implantation in Diabetic Patients", *Biosensors & Bioelectronics*, vol. 6, 1991, pp. 401-406.

Shichiri, M., et al., "Glycaemic Control in Pancreatectomized Dogs with a Wearable Artificial Endocrine Pancreas", *Diabetologia*, vol. 24, 1983, pp. 179-184.

Shichiri, M., et al., "In Vivo Characteristics of Needle-Type Glucose Sensor—Measurements of Subcutaneous Glucose Concentrations in Human Volunteers", *Hormone and Metabolic Research Supplement Series*, vol. 20, 1988, pp. 17-20.

Shichiri, M., et al., "Membrane Design for Extending the Long-Life of an Implantable Glucose Sensor", *Diabetes Nutrition and Metabolism*, vol. 2, 1989, pp. 309-313.

Shichiri, M., et al., "Needle-type Glucose Sensor for Wearable Artificial Endocrine Pancreas", *Implantable Sensors for Closed-Loop Prosthetic Systems*, Chapter 15, 1985, pp. 197-210.

Shichiri, M., et al., "Telemetry Glucose Monitoring Device With Needle-Type Glucose Sensor: A Useful Tool for Blood Glucose Monitoring in Diabetic Individuals", *Diabetes Care*, vol. 9, No. 3, 1986, pp. 298-301.

Shichiri, M., et al., "Wearable Artificial Endocrine Pancreas With Needle-Type Glucose Sensor", *The Lancet*, 1982, pp. 1129-1131.

Shults, M. C., et al., "A Telemetry-Instrumentation System for Monitoring Multiple Subcutaneously Implanted Glucose Sensors", *IEEE Transactions on Biomedical Engineering*, vol. 41, No. 10, 1994, pp. 937-942.

Sternberg, R., et al., "Study and Development of Multilayer Needle-Type Enzyme-Based Glucose Microsensors", *Biosensors*, vol. 4, 1988, pp. 27-40.

Thompson, M., et al., "In Vivo Probes: Problems and Perspectives", *Clinical Biochemistry*, vol. 19, 1986, pp. 255-261.

Turner, A., et al., "Diabetes Mellitus: Biosensors for Research and Management", *Biosensors*, vol. 1, 1985, pp. 85-115.

Updike, S. J., et al., "Principles of Long-Term Fully Implanted Sensors with Emphasis on Radiotelemetric Monitoring of Blood Glucose from Inside a Subcutaneous Foreign Body Capsule (FBC)", *Biosensors in the Body: Continuous in vivo Monitoring*, Chapter 4, 1997, pp. 117-137.

Velho, G., et al., "Strategies for Calibrating a Subcutaneous Glucose Sensor", *Biomedica Biochimica Acta*, vol. 48, 1989, pp. 957-964.

Wilson, G. S., et al., "Progress Toward the Development of an Implantable Sensor for Glucose", *Clinical Chemistry*, vol. 38, No. 9, 1992, pp. 1613-1617.

PCT Application No. PCT/US2010/032863, International Search Report and Written Opinion of the International Searching Authority mailed Jul. 7, 2010.

METHOD AND SYSTEM FOR PROVIDING REAL TIME ANALYTE SENSOR CALIBRATION WITH RETROSPECTIVE BACKFILL

RELATED APPLICATIONS

The present application claims priority under 35 U.S.C. §119(e) to U.S. provisional application No. 61/173,600 filed Apr. 29, 2009, entitled "Method and System for Providing Real Time Analyte Sensor Calibration with Retrospective Backfill", the disclosure of which is incorporated in its entirety by reference for all purposes.

BACKGROUND

Analyte, e.g., glucose monitoring systems including continuous and discrete monitoring systems generally include a small, lightweight battery powered and microprocessor controlled system which is configured to detect signals proportional to the corresponding measured glucose levels using an electrometer. RF signals may be used to transmit the collected data. One aspect of certain analyte monitoring systems include a transcutaneous or subcutaneous analyte sensor configuration which is, for example, at least partially positioned through the skin layer of a subject whose analyte level is to be monitored. The sensor may use a two or three-electrode (work, reference and counter electrodes) configuration driven by a controlled potential (potentiostat) analog circuit connected through a contact system.

An analyte sensor may be configured so that a portion thereof is placed under the skin of the patient so as to contact analyte of the patient, and another portion or segment of the analyte sensor may be in communication with the transmitter unit. The transmitter unit may be configured to transmit the analyte levels detected by the sensor over a wireless communication link such as an RF (radio frequency) communication link to a receiver/monitor unit. The receiver/monitor unit may perform data analysis, among other functions, on the received analyte levels to generate information pertaining to the monitored analyte levels.

SUMMARY

Devices and methods for analyte monitoring, e.g., glucose monitoring, and/or therapy management system including, for example, medication infusion device are provided. Embodiments include transmitting information from a first location to a second, e.g., using a telemetry system such as RF telemetry. Systems herein include continuous analyte monitoring systems, discrete analyte monitoring systems, and therapy management systems.

Embodiments include receiving sensor data from an analyte sensor of a sensor monitoring system, processing the received sensor data with time corresponding calibration data, outputting the processed sensor data, detecting one or more adverse conditions associated with the sensor monitoring system, disabling the output of the sensor data during an adverse condition time period, determining that the one or more detected adverse conditions is no longer present in the sensor monitoring system, retrieving the sensor data during the adverse condition time period, processing the retrieved sensor data during the adverse condition time period, and outputting the processed retrieved sensor data.

Embodiments include detecting a condition unsuitable for calibration of an analyte sensor for a predetermined time period, disabling output of information associated with the analyte sensor, determining a successful calibration of the analyte sensor, retrieving one or more parameters associated with the successful calibration, processing sensor data during the time period of disabled output of information with the one or more parameters associated with the successful calibration, and displaying the processed sensor data for the time period of disabled information output.

Embodiments include an interface configured to receive sensor data, a first memory configured to store the received sensor data, a processor coupled to the memory and configured to process the stored sensor data, a second memory coupled to the processor and configured to store the processed sensor data, and a display unit coupled to the second memory and configured to display the processed sensor data, where the processor is further configured to detect a condition unsuitable for calibration of a sensor for a predetermined time period, disable display of processed sensor data, determine a successful calibration of the sensor, retrieve one or more parameters associated with the successful calibration, process the sensor data during the time period of disabled display of sensor data with the one or more parameters associated with the successful calibration, and display the processed sensor data for the time period of disabled information output.

These and other objects, features and advantages of the present disclosure will become more fully apparent from the following detailed description of the embodiments, the appended claims and the accompanying drawings.

INCORPORATION BY REFERENCE

The following patents, applications and/or publications are incorporated herein by reference for all purposes: U.S. Pat. Nos. 4,545,382; 4,711,245; 5,262,035; 5,262,305; 5,264,104; 5,320,715; 5,509,410; 5,543,326; 5,593,852; 5,601,435; 5,628,890; 5,820,551; 5,822,715; 5,899,855; 5,918,603; 6,071,391; 6,103,033; 6,120,676; 6,121,009; 6,134,461; 6,143,164; 6,144,837; 6,161,095; 6,175,752; 6,270,455; 6,284,478; 6,299,757; 6,338,790; 6,377,894; 6,461,496; 6,503,381; 6,514,460; 6,514,718; 6,540,891; 6,560,471; 6,579,690; 6,591,125; 6,592,745; 6,600,997; 6,605,200; 6,605,201; 6,616,819; 6,618,934; 6,650,471; 6,654,625; 6,676,816; 6,730,200; 6,736,957; 6,746,582; 6,749,740; 6,764,581; 6,773,671; 6,881,551; 6,893,545; 6,932,892; 6,932,894; 6,942,518; 7,167,818; and 7,299,082; U.S. Published Application Nos. 2004/0186365; 2005/0182306; 2007/0056858; 2007/0068807; 2007/0227911; 2007/0233013; 2008/0081977; 2008/0161666; and 2009/0054748; U.S. patent application Ser. Nos. 11/831,866; 11/831,881; 11/831,895; 12/102,839; 12/102,844; 12/102,847; 12/102,855; 12/102,856; 12/152,636; 12/152,648; 12/152,650; 12/152,652; 12/152,657; 12/152,662; 12/152,670; 12/152,673; 12/363,712; 12/131,012; 12/242,823; 12/363,712; 12/393,921; 12/495,709; 12/698,124; 12/699,653; 12/699,844; 12/714,439; 12/761,372; and 12/761,387 and U.S. Provisional Application Ser. Nos. 61/230,686 and 61/227,967.

DETAILED DESCRIPTION

Figure 1:
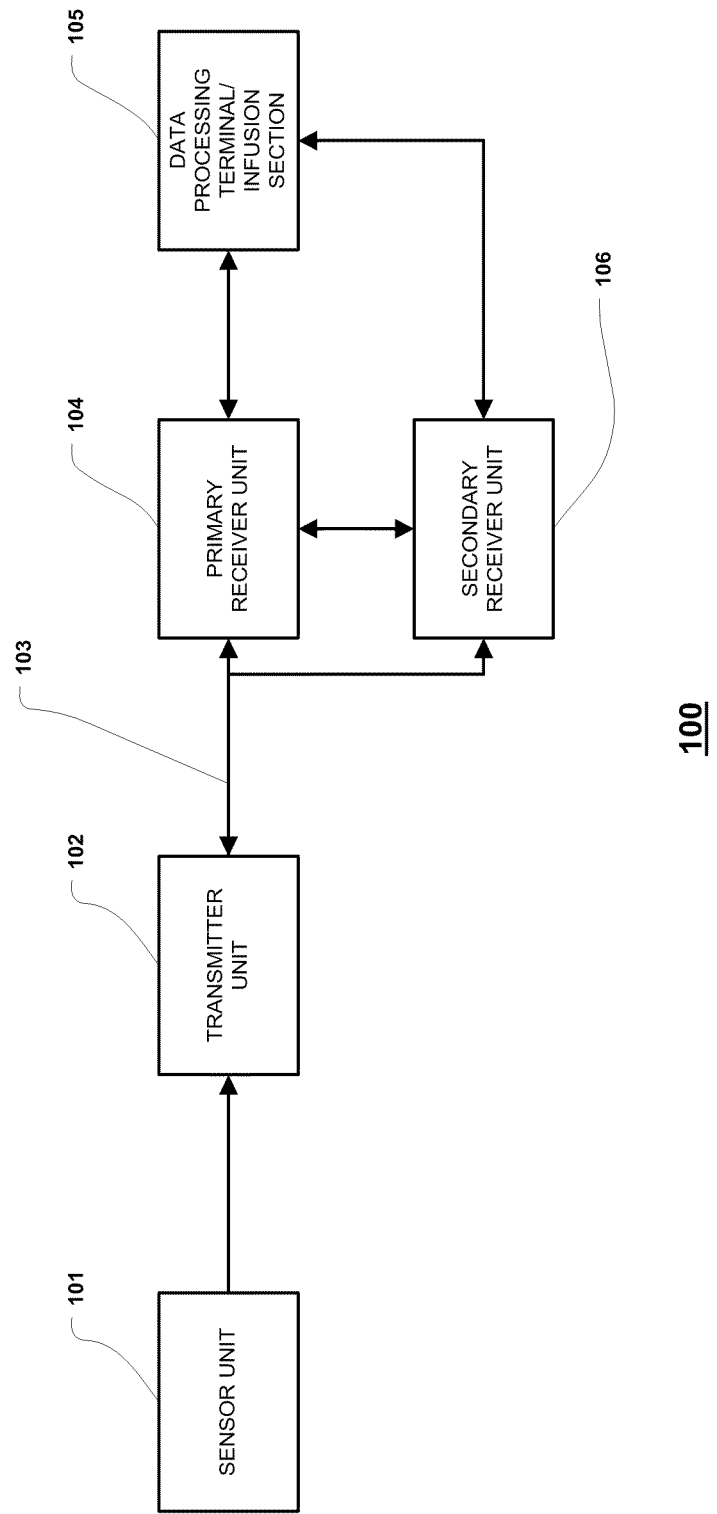
FIG. 1 illustrates a block diagram of a data monitoring and management system for practicing one or more embodiments of the present disclosure.

Before the present disclosure is described in additional detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. That the upper and lower limits of these smaller ranges may independently be included in the smaller ranges is also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise.

The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

The figures shown herein are not necessarily drawn to scale, with some components and features being exaggerated for clarity.

As described in further detail below, in accordance with the various embodiments of the present disclosure, there is provided a method and system for positioning a controller unit within a transmission range for close proximity communication, transmitting one or more predefined close proximity commands, and receiving a response packet in response to the transmitted one or more predefined close proximity commands. For example, in one aspect, close proximity communication includes short range wireless communication between communication components or devices, where the communication range is limited to about 10 inches or less, about 5 inches or less, or about 2 inches or less, or other suitable, short range or distance between the devices. The close proximity wireless communication in certain embodiments includes a bi-directional communication where a command sending communication device, when positioned within the short communication range or in close proximity to the command receiving communication device, is configured to transmit one or more commands to the command receiving communication device (for example, when a user activates or actuates a transmit command button or switch). In response, the command receiving communication device may be configured to perform one or more routines associated with the received command, and/or return or send back a response data packet or signal to the command sending communication device. Example of such functions and or commands may include, but not limited to activation of certain functions or routines such as analyte related data processing, and the like.

FIG. 1 illustrates a data monitoring and management system such as, for example, analyte (e.g., glucose) monitoring system 100 in accordance with one embodiment of the present disclosure. The subject invention is further described primarily with respect to a glucose monitoring system for convenience and such description is in no way intended to limit the scope of the invention. It is to be understood that the analyte monitoring system may be configured to monitor a variety of analytes, e.g., lactate, and the like.

Analytes that may be monitored include, for example, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored. More than one analyte may be monitored by a single system, e.g. a single analyte sensor.

The analyte monitoring system 100 includes a sensor unit 101, a data processing and transmitter unit 102 coupleable to the sensor unit 101, and a primary receiver unit 104 which is configured to communicate with the data processing and transmitter unit 102 via a bi-directional communication link 103. The primary receiver unit 104 may be further configured to transmit data to a data processing terminal 105 for evaluating the data received by the primary receiver unit 104. Moreover, the data processing terminal 105 in one embodiment may be configured to receive data directly from the data processing and transmitter unit 102 via a communication link which may optionally be configured for bi-directional communication. Accordingly, data processing and transmitter unit 102 and/or receiver unit 104 may include a transceiver.

Also shown in FIG. 1 is an optional secondary receiver unit 106 which is operatively coupled to the communication link and configured to receive data transmitted from the data processing and transmitter unit 102. Moreover, as shown in the Figure, the secondary receiver unit 106 is configured to communicate with the primary receiver unit 104 as well as the data processing terminal 105. Indeed, the secondary receiver unit 106 may be configured for bi-directional wireless communication with each or one of the primary receiver unit 104 and the data processing terminal 105. As discussed in further detail below, in one embodiment of the present disclosure, the secondary receiver unit 106 may be configured to include a limited number of functions and features as compared with the primary receiver unit 104. As such, the secondary receiver unit 106 may be configured substantially in a smaller compact housing or embodied in a device such as a wrist watch, pager, mobile phone, PDA, for example. Alternatively, the secondary receiver unit 106 may be configured with the same or substantially similar functionality as the primary receiver unit 104. The receiver unit may be configured to be used in conjunction with a docking cradle unit, for example for one or more of the following or other functions: placement by bedside, for re-charging, for data management, for night time monitoring, and/or bi-directional communication device.

In one aspect sensor unit 101 may include two or more sensors, each configured to communicate with data processing and transmitter unit 102. Furthermore, while only one data processing and transmitter unit 102, communication link 103, and data processing terminal 105 are shown in the embodiment of the analyte monitoring system 100 illustrated in FIG. 1, it will be appreciated by one of ordinary skill in the art that the analyte monitoring system 100 may include one or more sensors, multiple transmitter units 102, communication links 103, and data processing terminals 105. Moreover, within the scope of the present disclosure, the analyte monitoring system 100 may be a continuous monitoring system, or semi-continuous, or a discrete monitoring system. In a multi-component environment, each device is configured to be uniquely identified by each of the other devices in the system so that communication conflict is readily resolved between the various components within the analyte monitoring system 100.

In one embodiment of the present disclosure, the sensor unit 101 is physically positioned in or on the body of a user whose analyte level is being monitored. The sensor unit 101 may be configured to continuously sample the analyte level of the user and convert the sampled analyte level into a corresponding data signal for transmission by the data processing and transmitter unit 102. In certain embodiments, the data processing and transmitter unit 102 may be physically coupled to the sensor unit 101 so that both devices are integrated in a single housing and positioned on the user's body. The data processing and transmitter unit 102 may perform data processing such as filtering and encoding on data signals and/or other functions, each of which corresponds to a sampled analyte level of the user, and in any event data processing and transmitter unit 102 transmits analyte information to the primary receiver unit 104 via the communication link 103. Examples of such integrated sensor and transmitter units can be found in, among others, U.S. patent application Ser. No. 12/698,124, incorporated herein by reference.

In one embodiment, the analyte monitoring system 100 is configured as a one-way RF communication path from the data processing and transmitter unit 102 to the primary receiver unit 104. In such embodiment, the data processing and transmitter unit 102 transmits the sampled data signals received from the sensor unit 101 without acknowledgement from the primary receiver unit 104 that the transmitted sampled data signals have been received. For example, the data processing and transmitter unit 102 may be configured to transmit the encoded sampled data signals at a fixed rate (e.g., at one minute intervals) after the completion of the initial power on procedure. Likewise, the primary receiver unit 104 may be configured to detect such transmitted encoded sampled data signals at predetermined time intervals. Alternatively, the analyte monitoring system 100 may be configured with a bi-directional RF (or otherwise) communication between the data processing and transmitter unit 102 and the primary receiver unit 104.

Additionally, in one aspect, the primary receiver unit 104 may include two sections. The first section is an analog interface section that is configured to communicate with the data processing and transmitter unit 102 via the communication link 103. In one embodiment, the analog interface section may include an RF receiver and an antenna for receiving and amplifying the data signals from the data processing and transmitter unit 102, which are thereafter, demodulated with a local oscillator and filtered through a band-pass filter. The second section of the primary receiver unit 104 is a data processing section which is configured to process the data signals received from the data processing and transmitter unit 102 such as by performing data decoding, error detection and correction, data clock generation, and data bit recovery.

In operation, upon completing the power-on procedure, the primary receiver unit 104 is configured to detect the presence of the data processing and transmitter unit 102 within its range based on, for example, the strength of the detected data signals received from the data processing and transmitter unit 102 and/or a predetermined transmitter identification information. Upon successful synchronization with the corresponding data processing and transmitter unit 102, the primary receiver unit 104 is configured to begin receiving from the data processing and transmitter unit 102 data signals corresponding to the user's detected analyte level. More specifically, the primary receiver unit 104 in one embodiment is configured to perform synchronized time hopping with the corresponding synchronized data processing and transmitter unit 102 via the communication link 103 to obtain the user's detected analyte level.

Referring again to FIG. 1, the data processing terminal 105 may include a personal computer, a portable computer such as a laptop or a handheld device (e.g., personal digital assistants (PDAs)), and the like, each of which may be configured for data communication with the receiver via a wired or a wireless connection. Additionally, the data processing terminal 105 may further be connected to a data network (not shown) for storing, retrieving and updating data corresponding to the detected analyte level of the user.

Within the scope of the present disclosure, the data processing terminal 105 may include an infusion device such as an insulin infusion pump (external or implantable) or the like, which may be configured to administer insulin to patients, and which may be configured to communicate with the receiver unit 104 for receiving, among others, the measured analyte level. Alternatively, the receiver unit 104 may be configured to integrate or otherwise couple to an infusion device therein so that the receiver unit 104 is configured to administer insulin therapy to patients, for example, for administering and modifying basal profiles, as well as for determining appropriate boluses for administration based on, among others, the detected analyte levels received from the data processing and transmitter unit 102.

Additionally, the data processing and transmitter unit 102, the primary receiver unit 104 and the data processing terminal 105 may each be configured for bi-directional wireless communication such that each of the data processing and transmitter unit 102, the primary receiver unit 104 and the data processing terminal 105 may be configured to communicate (that is, transmit data to and receive data from) with each other via the wireless communication link 103. More specifically, the data processing terminal 105 may in one embodiment be configured to receive data directly from the data processing and transmitter unit 102 via a communication link, where the communication link, as described above, may be configured for bi-directional communication.

In this embodiment, the data processing terminal 105 which may include an insulin pump, may be configured to receive the analyte signals from the data processing and transmitter unit 102, and thus, incorporate the functions of the receiver 104 including data processing for managing the patient's insulin therapy and analyte monitoring. In one embodiment, the communication link 103 may include one or more of an RF communication protocol, an infrared communication protocol, a Bluetooth® enabled communication protocol, an 802.11x wireless communication protocol, or an equivalent wireless communication protocol which would allow secure, wireless communication of several units (for example, per HIPAA requirements) while avoiding potential data collision and interference.

Figure 2:
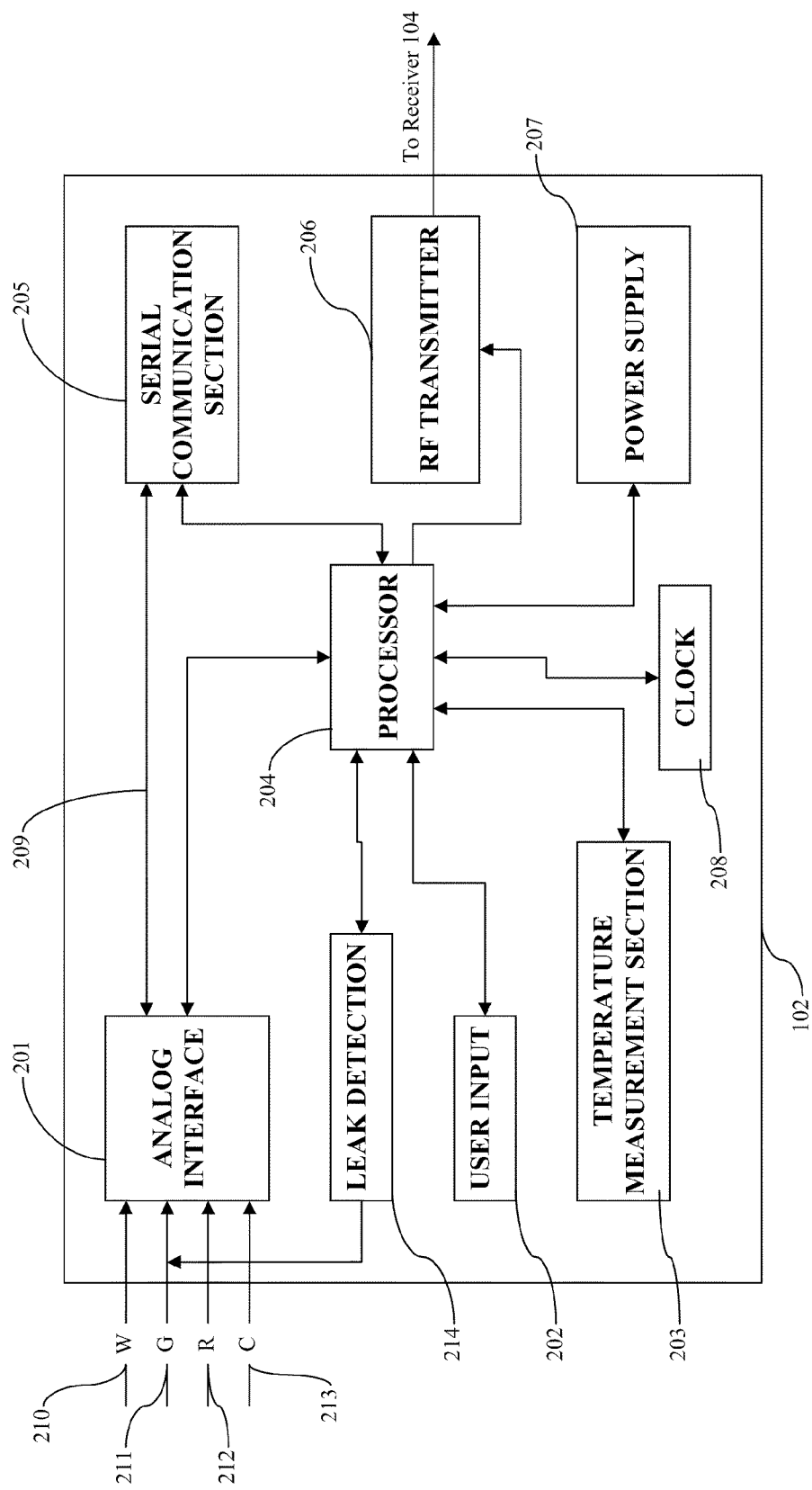
FIG. 2 is a block diagram of the transmitter unit of the data monitoring and management system shown in FIG. 1 in accordance with one embodiment of the present disclosure.

FIG. 2 is a block diagram of the transmitter of the data monitoring and detection system shown in FIG. 1 in accordance with one embodiment of the present disclosure. Referring to the Figure, the data processing and transmitter unit 102 in one embodiment includes an analog interface 201 configured to communicate with the sensor unit 101 (FIG. 1), a user input 202, and a temperature measurement section 203, each of which is operatively coupled to a transmitter processor 204 such as a central processing unit (CPU). As can be seen from FIG. 2, there are provided four contacts, three of which are electrodes—work electrode (W) 210, guard contact (G) 211, reference electrode (R) 212, and counter electrode (C) 213, each operatively coupled to the analog interface 201 of the data processing and transmitter unit 102 for connection to the sensor unit 101 (FIG. 1). In one embodiment, each of the work electrode (W) 210, guard contact (G) 211, reference electrode (R) 212, and counter electrode (C) 213 may be made using a conductive material that is either printed or etched or ablated, for example, such as carbon which may be printed, or a metal such as a metal foil (e.g., gold) or the like, which may be etched or ablated or otherwise processed to provide one or more electrodes. Fewer or greater electrodes and/or contact may be provided in certain embodiments.

Further shown in FIG. 2 are a transmitter serial communication section 205 and an RF transmitter 206, each of which is also operatively coupled to the transmitter processor 204. Moreover, a power supply 207 such as a battery is also provided in the data processing and transmitter unit 102 to provide the necessary power for the data processing and transmitter unit 102. In certain embodiments, the power supply 207 also provides the power necessary to power the sensor 101. In other embodiments, the sensor is a self-powered sensor, such as the sensor described in U.S. patent application Ser. No. 12/393,921, incorporated herein by reference. Additionally, as can be seen from the Figure, clock 208 is provided to, among others, supply real time information to the transmitter processor 204.

In one embodiment, a unidirectional input path is established from the sensor unit 101 (FIG. 1) and/or manufacturing and testing equipment to the analog interface 201 of the data processing and transmitter unit 102, while a unidirectional output is established from the output of the RF transmitter 206 of the data processing and transmitter unit 102 for transmission to the primary receiver unit 104. In this manner, a data path is shown in FIG. 2 between the aforementioned unidirectional input and output via a dedicated link 209 from the analog interface 201 to serial communication section 205, thereafter to the processor 204, and then to the RF transmitter 206. As such, in one embodiment, via the data path described above, the data processing and transmitter unit 102 is configured to transmit to the primary receiver unit 104 (FIG. 1), via the communication link 103 (FIG. 1), processed and encoded data signals received from the sensor unit 101 (FIG. 1). Additionally, the unidirectional communication data path between the analog interface 201 and the RF transmitter 206 discussed above allows for the configuration of the data processing and transmitter unit 102 for operation upon completion of the manufacturing process as well as for direct communication for diagnostic and testing purposes.

As discussed above, the transmitter processor 204 is configured to transmit control signals to the various sections of the data processing and transmitter unit 102 during the operation of the data processing and transmitter unit 102. In one embodiment, the transmitter processor 204 also includes a memory (not shown) for storing data such as the identification information for the data processing and transmitter unit 102, as well as the data signals received from the sensor unit 101. The stored information may be retrieved and processed for transmission to the primary receiver unit 104 under the control of the transmitter processor 204. Furthermore, the power supply 207 may include a commercially available battery, which may be a rechargeable battery.

In certain embodiments, the data processing and transmitter unit 102 is also configured such that the power supply section 207 is capable of providing power to the transmitter for a minimum of about three months of continuous operation, e.g., after having been stored for about eighteen months such as stored in a low-power (non-operating) mode. In one embodiment, this may be achieved by the transmitter processor 204 operating in low power modes in the non-operating state, for example, drawing no more than approximately 1 μA of current. Indeed, in one embodiment, a step during the manufacturing process of the data processing and transmitter unit 102 may place the data processing and transmitter unit 102 in the lower power, non-operating state (i.e., post-manufacture sleep mode). In this manner, the shelf life of the data processing and transmitter unit 102 may be significantly improved. Moreover, as shown in FIG. 2, while the power supply unit 207 is shown as coupled to the processor 204, and as such, the processor 204 is configured to provide control of the power supply unit 207, it should be noted that within the scope of the present disclosure, the power supply unit 207 is configured to provide the necessary power to each of the components of the data processing and transmitter unit 102 shown in FIG. 2.

Referring back to FIG. 2, the power supply section 207 of the data processing and transmitter unit 102 in one embodiment may include a rechargeable battery unit that may be recharged by a separate power supply recharging unit (for example, provided in the receiver unit 104) so that the data processing and transmitter unit 102 may be powered for a longer period of usage time. Moreover, in one embodiment, the data processing and transmitter unit 102 may be configured without a battery in the power supply section 207, in which case the data processing and transmitter unit 102 may be configured to receive power from an external power supply source (for example, a battery) as discussed in further detail below.

Referring yet again to FIG. 2, the temperature measurement section 203 of the data processing and transmitter unit 102 is configured to monitor the temperature of the skin near the sensor insertion site. The temperature reading is used to adjust the analyte readings obtained from the analog interface 201. In certain embodiments, the RF transmitter 206 of the transmitter unit 102 may be configured for operation in the frequency band of approximately 315 MHz to approximately 322 MHz, for example, in the United States. In certain embodiments, the RF transmitter 206 of the transmitter unit 102 may be configured for operation in the frequency band of approximately 400 MHz to approximately 470 MHz. Further, in one embodiment, the RF transmitter 206 is configured to modulate the carrier frequency by performing Frequency Shift Keying and Manchester encoding. In one embodiment, the data transmission rate is about 19,200 symbols per second, with a minimum transmission range for communication with the primary receiver unit 104.

Referring yet again to FIG. 2, also shown is a leak detection circuit 214 coupled to the guard contact (G) 211 and the processor 204 in the transmitter unit 102 of the data monitoring and management system 100. The leak detection circuit 214 in accordance with one embodiment of the present disclosure may be configured to detect leakage current in the sensor unit 101 to determine whether the measured sensor data are corrupt or whether the measured data from the sensor 101 is accurate. Exemplary analyte systems that may be employed are described in, for example, U.S. Pat. Nos. 6,134,461, 6,175,752, 6,121,611, 6,560,471, 6,746,582, and elsewhere, the disclosure of each of which are incorporated by reference for all purposes.

Figure 3:
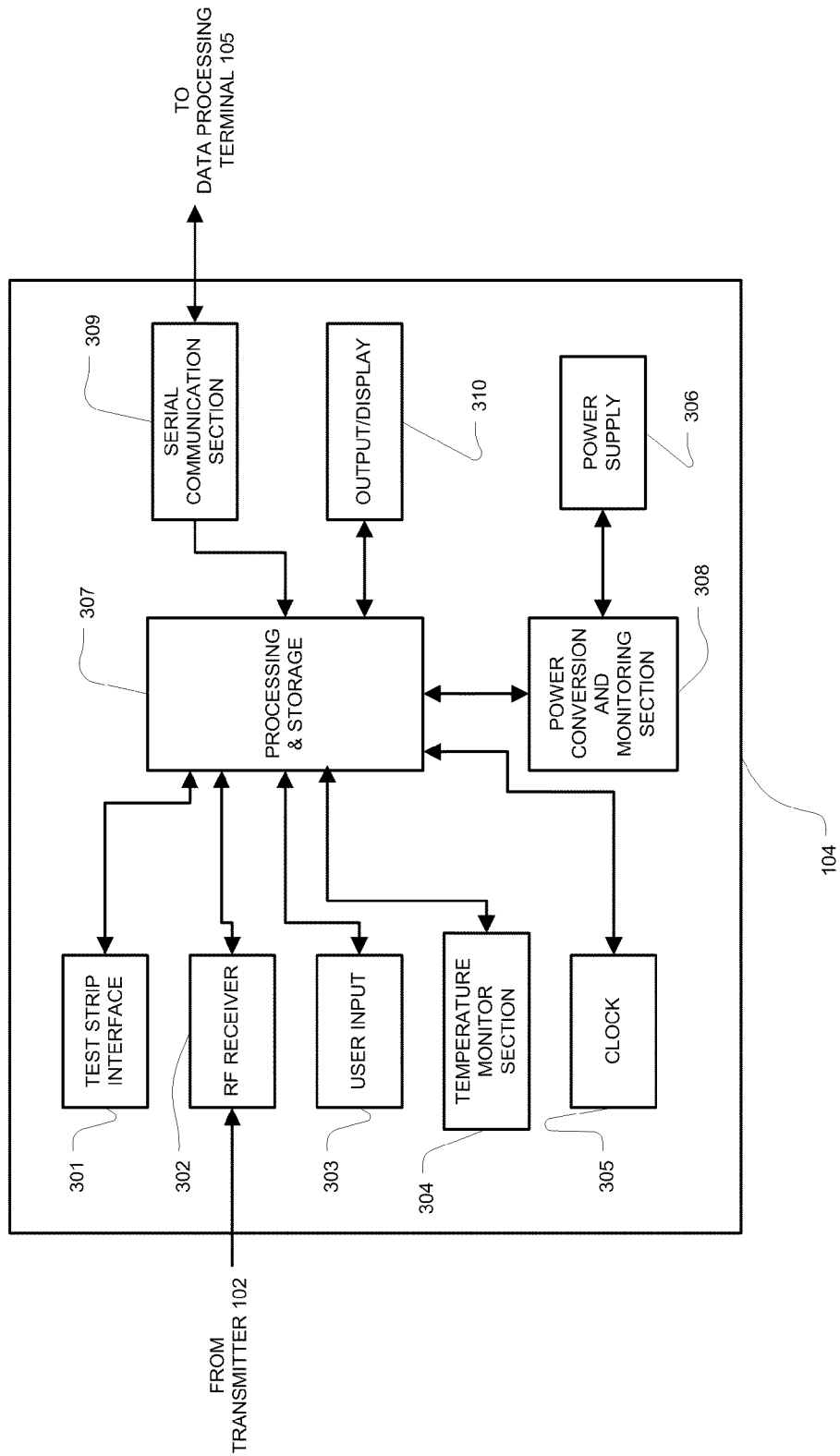
FIG. 3 is a block diagram of the receiver/monitor unit of the data monitoring and management system shown in FIG. 1 in accordance with one embodiment of the present disclosure.

FIG. 3 is a block diagram of the receiver/monitor unit of the data monitoring and management system shown in FIG. 1 in accordance with one embodiment of the present disclosure. Referring to FIG. 3, the primary receiver unit 104 includes an analyte test strip, e.g., blood glucose test strip, interface 301, an RF receiver 302, an input 303, a temperature monitor section 304, and a clock 305, each of which is operatively coupled to a receiver processor 307. As can be further seen from the Figure, the primary receiver unit 104 also includes a power supply 306 operatively coupled to a power conversion and monitoring section 308. Further, the power conversion and monitoring section 308 is also coupled to the receiver processor 307. Moreover, also shown are a receiver serial communication section 309, and an output 310, each operatively coupled to the receiver processor 307.

In one embodiment, the test strip interface 301 includes a glucose level testing portion to receive a manual insertion of a glucose test strip, and thereby determine and display the glucose level of the test strip on the output 310 of the primary receiver unit 104. This manual testing of glucose may be used to calibrate the sensor unit 101 or otherwise. The RF receiver 302 is configured to communicate, via the communication link 103 (FIG. 1) with the RF transmitter 206 of the transmitter unit 102, to receive encoded data signals from the transmitter unit 102 for, among others, signal mixing, demodulation, and other data processing. The input 303 of the primary receiver unit 104 is configured to allow the user to enter information into the primary receiver unit 104 as needed. In one aspect, the input 303 may include one or more keys of a keypad, a touch-sensitive screen, or a voice-activated input command unit. The temperature monitor section 304 is configured to provide temperature information of the primary receiver unit 104 to the receiver processor 307, while the clock 305 provides, among others, real time information to the receiver processor 307.

Each of the various components of the primary receiver unit 104 shown in FIG. 3 is powered by the power supply 306 which, in one embodiment, includes a battery. Furthermore, the power conversion and monitoring section 308 is configured to monitor the power usage by the various components in the primary receiver unit 104 for effective power management and to alert the user, for example, in the event of power usage which renders the primary receiver unit 104 in sub-optimal operating conditions. An example of such sub-optimal operating condition may include, for example, operating the vibration output mode (as discussed below) for a period of time thus substantially draining the power supply 306 while the processor 307 (thus, the primary receiver unit 104) is turned on. Moreover, the power conversion and monitoring section 308 may additionally be configured to include a reverse polarity protection circuit such as a field effect transistor (FET) configured as a battery activated switch.

The serial communication section 309 in the primary receiver unit 104 is configured to provide a bi-directional communication path from the testing and/or manufacturing equipment for, among others, initialization, testing, and configuration of the primary receiver unit 104. Serial communication section 309 can also be used to upload data to a computer, such as time-stamped blood glucose data. The communication link with an external device (not shown) can be made, for example, by cable, infrared (IR) or RF link. The output 310 of the primary receiver unit 104 is configured to provide, among others, a graphical user interface (GUI) such as a liquid crystal display (LCD) for displaying information. Additionally, the output 310 may also include an integrated speaker for outputting audible signals as well as to provide vibration output as commonly found in handheld electronic devices, such as mobile telephones presently available. In a further embodiment, the primary receiver unit 104 also includes an electro-luminescent lamp configured to provide backlighting to the output 310 for output visual display in dark ambient surroundings.

Referring back to FIG. 3, the primary receiver unit 104 in one embodiment may also include a storage section such as a programmable, non-volatile memory device as part of the processor 307, or provided separately in the primary receiver unit 104, operatively coupled to the processor 307. The processor 307 may be configured to synchronize with a transmitter, e.g., using Manchester decoding or the like, as well as error detection and correction upon the encoded data signals received from the transmitter unit 102 via the communication link 103.

Periodic calibration of the sensor unit 101 (FIG. 1) of an analyte monitoring system 100, in some embodiments, may be required for accurate calculation of a user's analyte level. Calibration, in some aspects, is used to ensure the analyte related data signals received at a transmitter unit 102 (and further transmitted to a receiver unit, such as the primary receiver unit 104) are correctly converted to corresponding analyte levels. Exemplary calibration protocols, routines and techniques are described, for example, in U.S. Pat. No. 7,299,082, U.S. patent application Ser. No. 11/537,991 filed Oct. 2, 2006, U.S. patent application Ser. No. 12/363,706 filed Jan. 30, 2009 and in U.S. patent application Ser. No. 12/363,712 filed Jan. 30, 2009, the disclosures of each of which are herein incorporated by reference for all purposes.

There are time periods where the sensor characteristics or the user's physiological condition renders the condition unsuitable for a sensor calibration event. For example, the sensor may be configured for periodic calibration, such as, after 2 hours after insertion, 10 hours after insertion, 12 hours after insertion, 24 hours after insertion, 48 hours after insertion, or 72 hours after insertion, or one or more combinations thereof. If a predetermined calibration event is triggered but a successful calibration does not result, after a certain time period (for example, a predetermined grace period during which to calibrate), the receiver unit may no longer display the monitored and processed glucose information.

Other conditions may also result in rendering the condition unsuitable for sensor calibration including, but not limited to, detection of a failure mode of a sensor, sensor data values being outside a predetermined range, rate of change of sensor data values being above a predetermined threshold, a temperature measurement outside a predetermined range, or any combination thereof.

Figure 4:
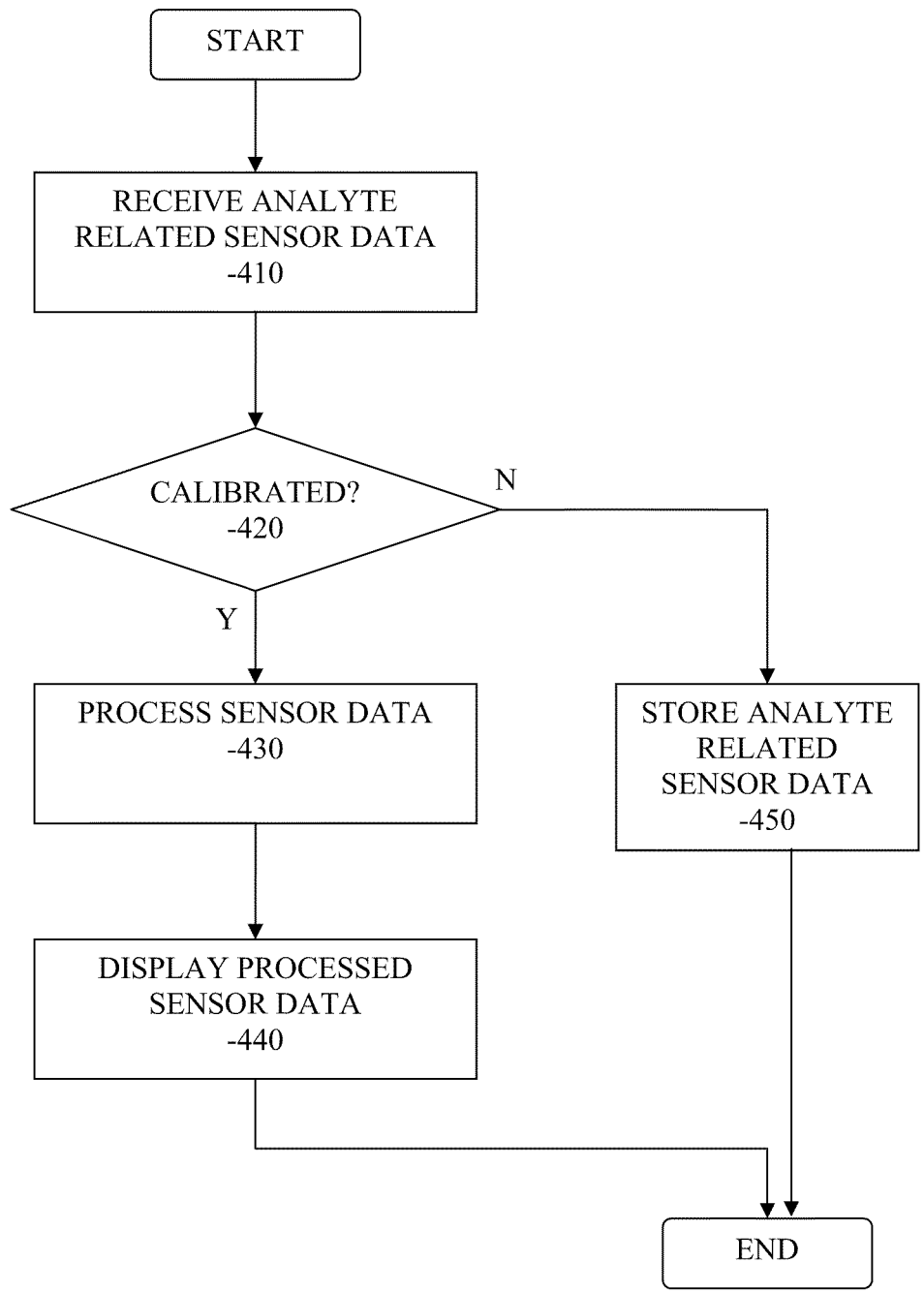
FIG. 4 illustrates analyte sensor data processing in accordance with one embodiment of the present disclosure.

FIG. 4 illustrates analyte sensor data processing in accordance with one embodiment of the present disclosure. Referring to FIG. 4, a transmitter unit 102 (FIG. 1) in operational contact with a sensor 101 receives analyte related sensor data (410) corresponding to a measured level of a biological fluid of the user. For example, the sensor 101 (FIG. 1) may be an analyte sensor configured to detect and measure the concentration of an analyte in a biological fluid, such as the blood of a user. Upon receipt of the analyte related sensor data, the transmitter unit 102 further transmits the analyte related sensor data to a receiver unit, such as primary receiver unit 104 (FIG. 1). It is to be noted that the reference to analyte related sensor data herein and throughout specification includes, for example, current signal received from the analyte sensor, as well as the current signal which has undergone a predetermined data processing routine including, for example, filtering, clipping, digitizing, and/or encoding, and/or any other further processing and/or conditioning. In one aspect, the primary receiver unit 104 determines whether the sensor is calibrated and is in acceptable condition for further data processing (420). When sensor related conditions are unsuitable for calibration, the analyte related sensor data is stored (450) in a memory, for example, in the primary receiver unit 104.

Referring still to FIG. 4, if the sensor data is calibrated and in condition for further data processing, the sensor data is further processed (430) and output for display (440) to a user on a display unit 310 (FIG. 3) of the primary receiver unit 104. In one embodiment, the display of the processed sensor data comprises a graphical representation of the processed sensor data. In other embodiments, the processed sensor data may be displayed as numerical values, visual indicators, auditory outputs, or combinations thereof. In one aspect, the processing routine described in conjunction with FIG. 4 is performed or executed in, for example, the transmitter unit 102, the secondary receiver unit 106 (FIG. 1), or the data processing terminal 105 (FIG. 1) of the analyte monitoring system 100 (FIG. 1) based on analyte data received from the sensor 101.

Figure 5:
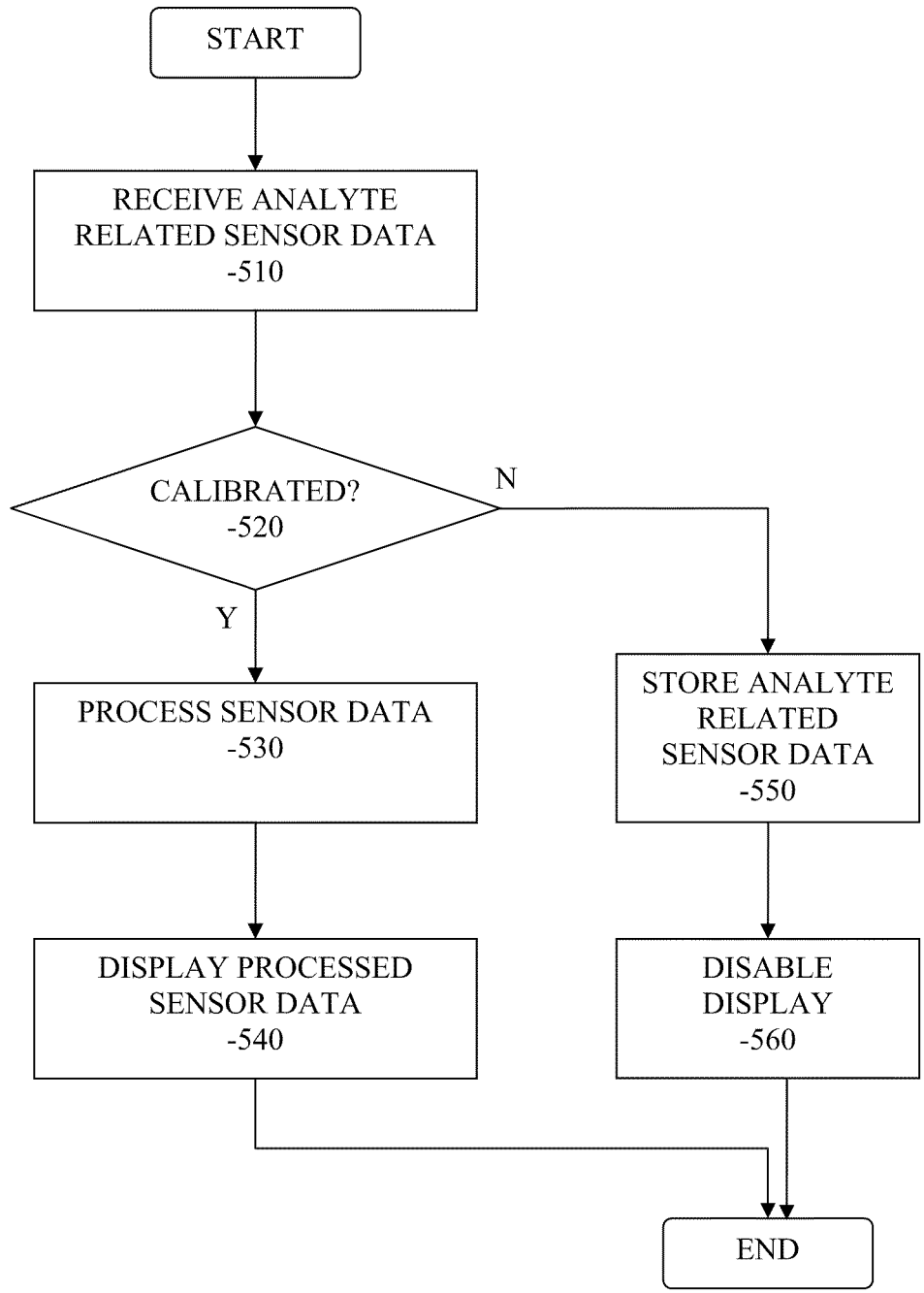
FIG. 5 illustrates analyte sensor data processing in accordance with one embodiment of the present disclosure.

FIG. 5 illustrates analyte sensor data processing in accordance with one embodiment of the present disclosure. Referring to FIG. 5, in one embodiment, transmitter unit 102 (FIG. 1) receives analyte related sensor data (510) from a sensor 101 (FIG. 1). Upon receipt of the analyte related sensor data, the transmitter unit 102 transmits the analyte related sensor data (or processed, digitized, and/or filtered signals) to the primary receiver unit 104 (FIG. 1). The primary receiver unit 104 is configured to determine if calibration of the sensor data is suitable—that is, whether the conditions necessary for sensor calibration are met (520).

Still referring to FIG. 5, if it is determined that the sensor 101 is not calibrated or calibration condition for calibrating the sensor 101 is not met, in one aspect, the primary receiver unit stores the analyte related sensor data in a memory (550) and temporarily disables display of the sensor data (560) to the user (for example, if a calibration event has not occurred and the calibration grace period has expired). On the other hand, if the sensor 101 is calibrated, the sensor data is processed (530) by the primary receiver unit 104 and the processed sensor data is output to the user (540), for example via a display unit 310 (FIG. 3) of the primary receiver unit 104. In one aspect, the processing routine described in conjunction with FIG. 5 is performed or executed in, for example, the transmitter unit 102, the secondary receiver unit 106, or the data processing terminal 105 of the analyte monitoring system 100 based on analyte data received from the sensor 101 (FIG. 1).

Figure 7A:
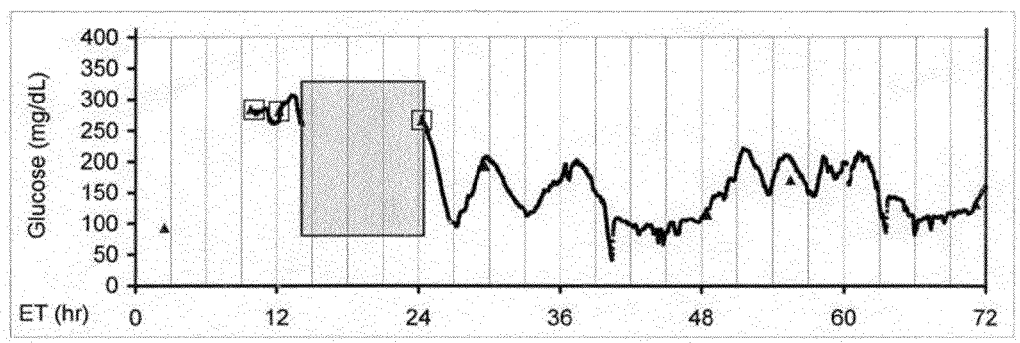
FIGS. 7A and 7B illustrate backfill of gaps of a period of uncalibrated sensor data in one embodiment.

In one aspect, the display or output of processed sensor data may be disabled if a required calibration event is unsuccessful over a permitted time period (for example, including a predetermined grace period measured from the scheduled calibration). Thereafter, upon successful calibration, the system resumes display of the processed and calibrated analyte sensor data. However, there may be a time period or a gap in the output display during which the necessary calibration did not occur in a timely manner. For example, as shown in FIG. 7A, if sensor data is displayed as a graphical display, during time periods where the analyte monitoring system 100 was not properly calibrated, analyte related sensor data was not processed and/or displayed, resulting in a gap in the graphical display.

Figure 6:
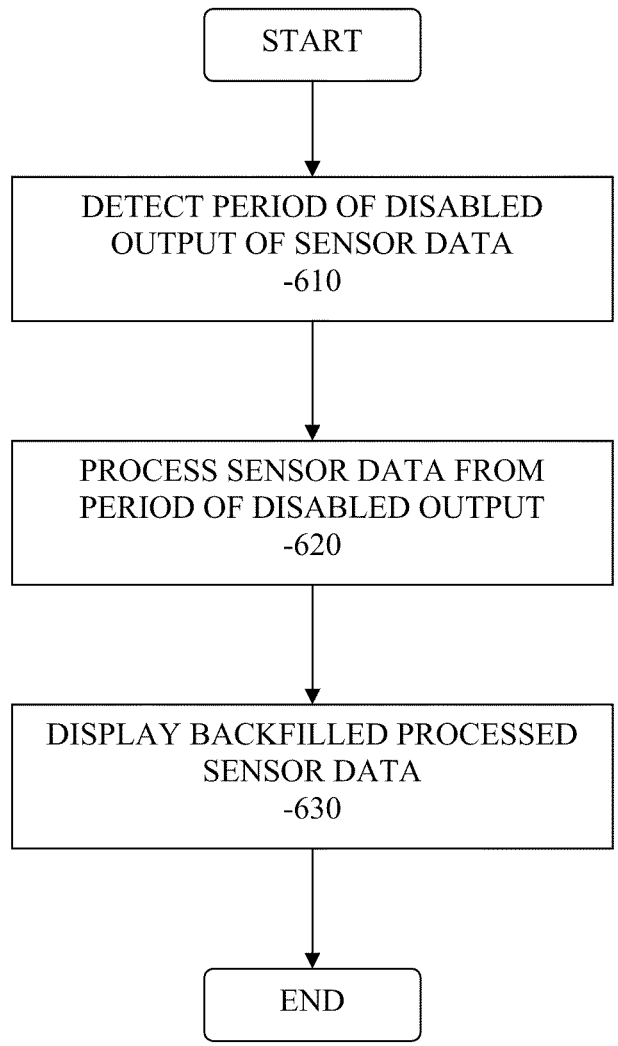
FIG. 6 illustrates backfilling gaps in sensor data in one embodiment of the present disclosure.

FIG. 6 illustrates backfilling gaps in sensor data in one embodiment of the present disclosure. Referring to FIG. 6, when a scheduled calibration event fails and the associated grace period for calibration does not occur, the output display of the processed, calibrated sensor data is disabled (610). Referring to FIG. 6, once the system recovers after a successful calibration event, the calibrated sensor data is once again displayed (and stored). Furthermore, in one aspect, based on the parameters associated with the successful calibration, the previously unprocessed data during the display time out period may be retrieved (for example, the previously stored analyte related sensor signals during this period) and processed using calibration data, such as a sensitivity ratio for conversion of analyte related sensor data to analyte levels. For example, in one aspect, the subset of analyte related sensor data that were previously unprocessed or uncalibrated due to unsuccessful contemporaneous calibration may be processed using, for example, calibration data such as the sensitivity ratio determined from the most recent successful calibration event, and thereafter, the gap in output display illustrating the processed and calibrated signals may be filled.

Figure 7B:
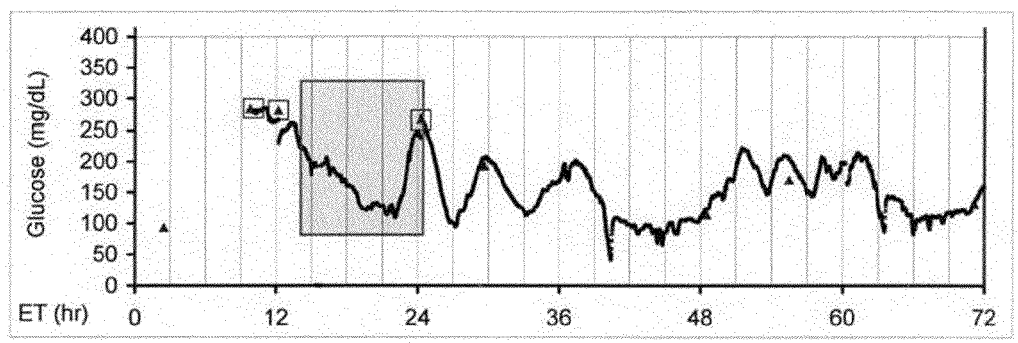

In one aspect, once successful calibration of the sensor data occurs, the calibration parameters from this calibration event may be used to process the sensor data during the period of disabled output or display (620). Upon successful processing of the sensor data during the period of disabled output, the processed sensor data during this time period is backfilled, or the gap in the processed continuous sensor data are filled in the display (630). By way of an example, FIGS. 7A and 7B illustrate the replacement of a period of unprocessed sensor data with corresponding backfilled processed sensor data, in one embodiment.

In one embodiment, the backfilled processed sensor data is displayed immediately upon calculation. In another embodiment, the backfilled processed sensor data is not displayed immediately, but rather, after waiting a predetermined period of time. The backfilled processed sensor data may not be displayed immediately to avoid possible unnecessary or incorrect action by a user in response to the backfilled processed sensor data. In this manner, in one aspect, the user or a healthcare provider may be provided with a continuous set of analyte data from the analyte monitoring system without any gaps in the processed signals for further analysis and/or therapy management.

In this manner, in accordance with the embodiments of the present disclosure, gaps in monitored analyte levels using an analyte monitoring system due to, for example, inability to promptly calibrate the sensor, system malfunction, sensor dislodging, signal errors associated with the sensor, transmitter unit, receiver unit, and the like, or any other variables or parameters that result in the inability of the analyte monitoring system to display or output the real-time monitored analyte level, may be retrospectively filled or reprocessed so that the data gap is closed and the continuously monitored analyte level does not have any or substantially missing data. That is, in embodiments of the present disclosure, upon correction or rectification of the condition or conditions/parameters which resulted in the analyte monitoring system disabling the output results associated with the monitored real time analyte levels, the parameters associated with the correction or rectification may be used to retrospectively correct or process data or signals so that the missing gaps in analyte related data may be processed and backfilled.

In this manner, advantageously, in aspects of the present disclosure, additional robustness may be provided to the user and/or the healthcare provider to improve therapy or health management decisions.

In one embodiment, a method may include receiving sensor data from an analyte sensor of a sensor monitoring system, processing the received sensor data with time corresponding calibration data, outputting the processed sensor data, detecting one or more adverse conditions associated with the sensor monitoring system, disabling the output of the sensor data during an adverse condition time period, determining that the one or more detected adverse conditions is no longer present in the sensor monitoring system, retrieving the sensor data during the adverse condition time period, processing the retrieved sensor data during the adverse condition time period, and outputting the processed retrieved sensor data.

In one aspect, outputting the processed sensor data may include displaying the sensor data in one or more of a graphical, numerical, pictorial, audible, vibratory, or one or more combinations thereof.

The one or more detected adverse conditions may include one or more of a sensor instability condition, a calibration failure condition, or a monitoring system failure condition.

The sensor instability condition may include one or more of an early signal attenuation condition of the sensor, sensor misposition error, sensor communication error, temperature measurement outside a predetermined range, or a combination thereof.

The calibration failure condition may include one or more of an analyte level exceeding a predetermined threshold, a rate of change of analyte level exceeding a predetermined threshold, a signal error associated with the reference data, a data unavailability condition, or a combination thereof.

Furthermore, the method may include storing the processed sensor data with the associated time information based on the analyte level detection time by the sensor.

In another embodiment, a method may include detecting a condition unsuitable for calibration of an analyte sensor for a predetermined time period, disabling output of information associated with the analyte sensor, determining a successful calibration of the analyte sensor, retrieving one or more parameters associated with the successful calibration, processing sensor data during the time period of disabled output of information with the one or more parameters associated with the successful calibration, and displaying the processed sensor data for the time period of disabled information output.

The sensor data may be analyte concentration data.

The analyte concentration data may include blood glucose concentration data.

The sensor data may be processed in substantially real-time.

The condition unsuitable for calibration may include one or more of a failure mode of a sensor, sensor data outside a predetermined acceptable range, a rate of change of sensor data above a predetermined level, a requirement for calibration of a sensor, a temperature measurement outside a predetermined range, or any combination thereof.

The processed sensor data for the time period of disabled information output may be displayed immediately upon processing.

The processed sensor data for the time period of disabled information output may be displayed only after waiting a predetermined period of time.

In another embodiment, an apparatus may include an interface configured to receive sensor data, a first memory configured to store the received sensor data, a processor coupled to the memory and configured to process the stored sensor data, a second memory coupled to the processor and configured to store the processed sensor data, and a display unit coupled to the second memory and configured to display the processed sensor data, wherein the processor is further configured to detect a condition unsuitable for calibration of a sensor for a predetermined time period, disable display of processed sensor data, determine a successful calibration of the sensor, retrieve one or more parameters associated with the successful calibration, process the sensor data during the time period of disabled display of sensor data with the one or more parameters associated with the successful calibration, and display the processed sensor data for the time period of disabled information output.

The sensor may be an analyte sensor.

The analyte sensor may be a glucose sensor.

The sensor data may correspond to analyte concentration data.

The analyte concentration data may include blood glucose concentration data.

Furthermore, the apparatus may be configured to process and display the sensor data substantially in real-time.

In one aspect, the condition unsuitable for calibration may include one or more of a failure mode of a sensor, sensor data outside a predetermined acceptable range, a rate of change of sensor data above a predetermined level, a requirement for calibration of a sensor, a temperature measurement outside a predetermined range, or any combination thereof.

The display unit may be configured to display the processed sensor data for the time period of disabled information output substantially immediately upon processing the sensor data.

The display unit may be configured to display the processed sensor data for the time period of disabled information output only after waiting a predetermined period of time.

Various other modifications and alterations in the structure and method of operation of this invention will be apparent to those skilled in the art without departing from the scope and spirit of the invention. Although the invention has been described in connection with specific preferred embodiments, it should be understood that the invention as claimed should not be unduly limited to such specific embodiments. It is intended that the following claims define the scope of the present disclosure and that structures and methods within the scope of these claims and their equivalents be covered thereby.

What is claimed is:

1. A method, comprising:
  receiving sensor data from an analyte sensor of a sensor monitoring system;
  processing the received sensor data with time corresponding calibration data;
  outputting the processed sensor data;
  detecting one or more adverse conditions associated with the sensor monitoring system;
  disabling the output of the sensor data during an adverse condition time period;

storing sensor data received from the analyte sensor during the adverse condition time period;

determining that the one or more detected adverse conditions is no longer present in the sensor monitoring system;

retrieving the sensor data stored during the adverse condition time period after it is determined that the one or more detected adverse conditions is no longer present;

processing the retrieved sensor data stored during the adverse condition time period; and outputting the processed retrieved sensor data.

2. The method of claim 1, wherein outputting the processed sensor data includes displaying the sensor data in one or more of a graphical, numerical, pictorial, audible, vibratory, or one or more combinations thereof.

3. The method of claim 1, wherein the one or more detected adverse conditions includes one or more of a sensor instability condition, a calibration failure condition, or a monitoring system failure condition.

4. The method of claim 3, wherein the sensor instability condition includes one or more of an early signal attenuation condition of the sensor, sensor mis-position error, sensor communication error, temperature measurement outside a predetermined range, or a combination thereof.

5. The method of claim 3, wherein the calibration failure condition includes one or more of an analyte level exceeding a predetermined threshold, a rate of change of analyte level exceeding a predetermined threshold, a signal error associated with the reference data, a data unavailability condition, or a combination thereof.

6. The method of claim 1 including storing the processed sensor data with the associated time information based on the analyte level detection time by the sensor.

7. A method, comprising:

detecting a condition unsuitable for calibration of an analyte sensor for a predetermined time period;

disabling output of information associated with the analyte sensor;

storing sensor data received from the analyte sensor during a time period of disabled output of information;

determining a successful calibration of the analyte sensor;

retrieving one or more parameters associated with the successful calibration;

after the one or more parameters associated with successful calibration has been retrieved, processing the sensor data stored during the time period of disabled output of information with the one or more parameters associated with the successful calibration; and displaying the processed sensor data for the time period of disabled output of information.

8. The method of claim 7, wherein the sensor data is analyte concentration data.

9. The method of claim 8, wherein the analyte concentration data includes blood glucose concentration data.

10. The method of claim 7, wherein the sensor data is processed in substantially real-time.

11. The method of claim 7, wherein the condition unsuitable for calibration includes one or more of a failure mode of a sensor, sensor data outside a predetermined acceptable range, a rate of change of sensor data above a predetermined level, a requirement for calibration of a sensor, a temperature measurement outside a predetermined range, or any combination thereof.

12. The method of claim 7, wherein the processed sensor data for the time period of disabled information output is displayed substantially immediately upon processing.

13. The method of claim 7, wherein the processed sensor data for the time period of disabled information output is displayed only after waiting a predetermined period of time.

14. An apparatus, comprising:

an interface configured to receive sensor data;

a first memory configured to store the received sensor data;

a processor coupled to the first memory and configured to process the stored sensor data;

a second memory coupled to the processor and configured to store the processed sensor data; and a display unit coupled to the second memory and configured to display the processed sensor data;

wherein the processor is further configured to:

detect a condition unsuitable for calibration of a sensor for a predetermined time period;

disable a display of processed sensor data;

store sensor data received during a time period of disabled display in the first memory;

determine a successful calibration of the sensor;

retrieve one or more parameters associated with the successful calibration;

after the one or more parameters associated with successful calibration have been retrieved, process the sensor data stored during the time period of disabled display of sensor data with the one or more parameters associated with the successful calibration; and display the processed sensor data for the time period of disabled display.

15. The apparatus of claim 14, wherein the sensor is an analyte sensor.

16. The apparatus of claim 15, wherein the analyte sensor is a glucose sensor.

17. The apparatus of claim 15, wherein the sensor data corresponds to analyte concentration data.

18. The apparatus of claim 17, wherein the analyte concentration data includes blood glucose concentration data.

19. The apparatus of claim 14 configured to process and display the sensor data substantially in real-time.

20. The apparatus of claim 14, wherein the condition unsuitable for calibration includes one or more of a failure mode of a sensor, sensor data outside a predetermined acceptable range, a rate of change of sensor data above a predetermined level, a requirement for calibration of a sensor, a temperature measurement outside a predetermined range, or any combination thereof.

21. The apparatus of claim 14, wherein the display unit is configured to display the processed sensor data for the time period of disabled display substantially immediately upon processing the sensor data.

22. The apparatus of claim 14, wherein the display unit is configured to display the processed sensor data for the time period of disabled display only after waiting a predetermined period of time.

* * * * *